(12) United States Patent
Zumeris et al.

(10) Patent No.: US 9,028,748 B2
(45) Date of Patent: May 12, 2015

(54) SYSTEM AND METHOD FOR SURFACE ACOUSTIC WAVE TREATMENT OF MEDICAL DEVICES

(75) Inventors: Jona Zumeris, Haifa (IL); Harold Jacob, Cedarhurst, NY (US); Hanan Raskin, Kfar Saba (IL); Gera Kratysh, Haifa (IL); Yanina Zumeris, Haifa (IL)

(73) Assignee: NanoVibronix Inc, Cedarhurst, NY (US)

( * ) Notice: Subject to any disclaimer, the term of this patent is extended or adjusted under 35 U.S.C. 154(b) by 1231 days.

(21) Appl. No.: 11/710,616

(22) Filed: Feb. 26, 2007

(65) Prior Publication Data

US 2007/0213645 A1 Sep. 13, 2007

Related U.S. Application Data

(60) Provisional application No. 60/776,067, filed on Feb. 24, 2006.

(51) Int. Cl.
| | |
|---|---|
| *A61L 2/00* | (2006.01) |
| *A61L 2/025* | (2006.01) |
| *A61H 23/02* | (2006.01) |
| *A61L 2/24* | (2006.01) |
| *A61M 25/00* | (2006.01) |

(52) U.S. Cl.
CPC ............ *A61L 2/025* (2013.01); *A61H 23/0236* (2013.01); *A61L 2/24* (2013.01); *A61H 2201/105* (2013.01); *A61M 2025/0019* (2013.01)

(58) Field of Classification Search
USPC ......................................... 422/20; 623/11.11
See application file for complete search history.

(56) References Cited

U.S. PATENT DOCUMENTS

| | | | |
|---|---|---|---|
| 4,040,414 | A | 8/1977 | Suroff |
| 4,419,248 | A | 12/1983 | Costerton |
| 5,312,813 | A | 5/1994 | Costerton et al. |
| 5,366,505 | A | 11/1994 | Farber |

(Continued)

FOREIGN PATENT DOCUMENTS

| | | |
|---|---|---|
| JP | 03170172 | 7/1991 |
| WO | WO 03/099100 A2 | 12/2003 |
| WO | WO 2005/117156 | 12/2005 |

OTHER PUBLICATIONS

International Search Report from International Application No. PCT/US07/04849, mailed Feb. 6, 2008.

(Continued)

*Primary Examiner* — Thomas J Sweet
*Assistant Examiner* — Rebecca Preston
(74) *Attorney, Agent, or Firm* — Mark S. Cohen; Pearl Cohen Zedek Latzer Baratz LLP

(57) ABSTRACT

Methods and systems are provided for treatment of medical devices using surface acoustic waves (SAW) of Rayleigh, "pseudo" Rayleigh and Lamb type. In some embodiments, use of such SAW is controlled such that relative velocity of bacteria is achieved wherein the vibration amplitude of the bacteria is smaller than a Z-potential repulsive zone of the bacteria, thus preventing biofilm formation on the medical devices. In some embodiments, systems of the present invention are powered by body movements, and may also provide a feedback loop for control of parameters. In some embodiments, the medical devices of the present invention are comprised of piezoelectric material, and act as self-actuators for the system.

61 Claims, 18 Drawing Sheets

(56) References Cited

U.S. PATENT DOCUMENTS

| | | | |
|---|---|---|---|
| 5,462,644 | A | 10/1995 | Woodson |
| 5,505,945 | A | 4/1996 | Gristina et al. |
| 5,636,180 | A | 6/1997 | Grothaus et al. |
| 5,876,602 | A | 3/1999 | Jons et al. |
| 5,895,362 | A | 4/1999 | Elstrom et al. |
| 5,954,977 | A | 9/1999 | Miller et al. |
| 6,086,772 | A | 7/2000 | Tanimura et al. |
| 6,096,225 | A | 8/2000 | Yang et al. |
| 6,156,549 | A | 12/2000 | Drewes et al. |
| 6,326,177 | B1 | 12/2001 | Schoenbach et al. |
| 6,428,477 | B1 | 8/2002 | Mason |
| 6,428,491 | B1 | 8/2002 | Weiss |
| 6,433,244 | B1 | 8/2002 | Roe et al. |
| 7,165,451 | B1* | 1/2007 | Brooks et al. .................... 73/579 |
| 7,429,248 | B1 | 9/2008 | Winder et al. |
| 2002/0068866 | A1* | 6/2002 | Zikorus et al. ................ 600/424 |
| 2003/0177819 | A1 | 9/2003 | Maale |
| 2003/0236487 | A1 | 12/2003 | Knowlton |
| 2004/0027034 | A1 | 2/2004 | Kawaguchi et al. |
| 2004/0073267 | A1* | 4/2004 | Holzer ............................ 607/35 |
| 2004/0236268 | A1 | 11/2004 | Mitragotri et al. |
| 2004/0236269 | A1 | 11/2004 | Marchitto et al. |
| 2005/0038376 | A1* | 2/2005 | Zumeris et al. ................. 604/22 |
| 2005/0075599 | A1 | 4/2005 | Redding, Jr. |
| 2005/0095351 | A1 | 5/2005 | Zumeris et al. |
| 2005/0137656 | A1* | 6/2005 | Malak ............................. 607/88 |
| 2005/0200434 | A1 | 9/2005 | Takano |
| 2005/0267451 | A1 | 12/2005 | Black |
| 2005/0268921 | A1 | 12/2005 | Zumeris et al. |
| 2005/0283110 | A1 | 12/2005 | Atala et al. |
| 2006/0184071 | A1 | 8/2006 | Klopotek |
| 2007/0038156 | A1 | 2/2007 | Rosenberg |

OTHER PUBLICATIONS

International Search Report from International Application No. PCT/US07/04842, mailed Jun. 10, 2008.
U.S. Appl. No. 11/710,615, filed Feb. 26, 2007, Zumeris et al.
Maki DG, Tambyah PA; "Engineering Out the Risk of Infection with Urinary Catheters". Emerging Infectious Diseases; vol. 7, p. 1-6, 2001.
Gristina AG, "Biomaterial-Centered Infection: Microbial Adhesion Versus Tissue Intergration". Science 1987, 237: 1588-1595.
Schierholz JM and Beuth J. "Implant Infections: a Haven for Opportunistic Bacteria". 2001. J. Hosp. Infect. 49: 87-93.
Whiteley, M., Lee, K. M. & Greenberg, E. P. "Identification of Genes Controlled by Quorum Sensing in *Pseudomonas aeruginosa*". Proc. Natl Acad. Sci. USA 96, 13904-13909 (1999).
Lewis K. "Riddle of Biofilm Resistance". Antimicrob. Agents Chemother. 2001, 45, 999-1007.
Mahenthiralingam E., Campbell ME., Speert DP. "Nonmotility and Phagocytic Resistance of *Pseudomonas aeruginosa* Isolates from Chronically Colonized Patients with Cystic Fibrosis". Infect Immun. 1994, 62:596-605.
Thibon P., Le Coutour X., Leroyer R., Fabry J. Randomized Multi-Centre Trial of the Effects of a Catheter Coated with Hydrogel and Silver Salts on the Incidence of Hospital-Acquired Urinary Tract Infections.J. Hosp Infect. (2000) 45:117-1124.
Yamamoto AJ, Solomon JA, Soulen MC, Tang J, Parkinson K, Lin R, Schears GJ. "Sutureless Securement Device Reduces Complications of Peripherally Inserted Central Venous Catheters". J. Vasc Interv Radiol. 2002;13:77-81.
Rediske AM, Roeder BL, Nelson JL et al. "Pulsed Ultrasound Enhances the Killing of *Escherichia Coli* Biofilms by Aminoglycoside Antibiotics in Vivo". Antimicrobial Agents and Chemotherapy, Mar. 2000, p. 771-772.
Carmen JC, Roeder BL, Nelson JL, Ogilvie RL, Robison RA, Schaalje GB, Pitt WG. "Treatment of Biofilm Infections on Implants with Low-Frequency Ultrasound and Antibiotics" .Am J Infect Control. 2005, 33:78-82.
Schachter B. "Slimy Business—the Biotechnology of Biofilms", Nature Biothechnology, Apr. 2003; 21:361-365.
Trautner BW, Darouich RO, "Catheter Associated Infections Pathogenesis Affect Prevention", Archives of Internal Medicine, Apr. 2004; 164:842-850.
King D. "Diagnostic Ultrasound" Physical and Technical Principles p. 26-27, 1974.
Donlan R. "Biofilms: microbial life on surfaces" Emerging Infectious Diseases vol. 8, No. 9, p. 881-890, 2002.
Campbell C. "Surface Acoustic Wave Devices for Mobile and Wireless Communications" Academic Press Inc. p. 19-22, 1998.
Ueha S. et al. "Ultrasonic Motors Theory and Applications" Clarendon Press Oxford 1993.
Office Action for U.S. Appl. No. 11/710,615, dated Sep. 14, 2010.
Office Action for Chinese Application No. 200780014875.5, dated Sep. 8, 2010.
Office Action for Israeli Patent Application No. 193600 dated Nov. 10, 2011.
Office Action for U.S. Appl. No. 11/710,615 mailed Jul. 23, 2012.
Supplementary European Search Report for corresponding European Application No. EP 07861247, mailed Aug. 2, 2012.
Miyasaka et al (Ultrasonic Tissue Characterization of Photodamaged Skin by Scanning Acoustic Microscopy, Tokai J Exp Clin Med, vol. 30, No. 4, pp. 217-225, 2005.
Office Action for U.S. Appl. No. 11/710,615 dated Jan. 4, 2012.

* cited by examiner

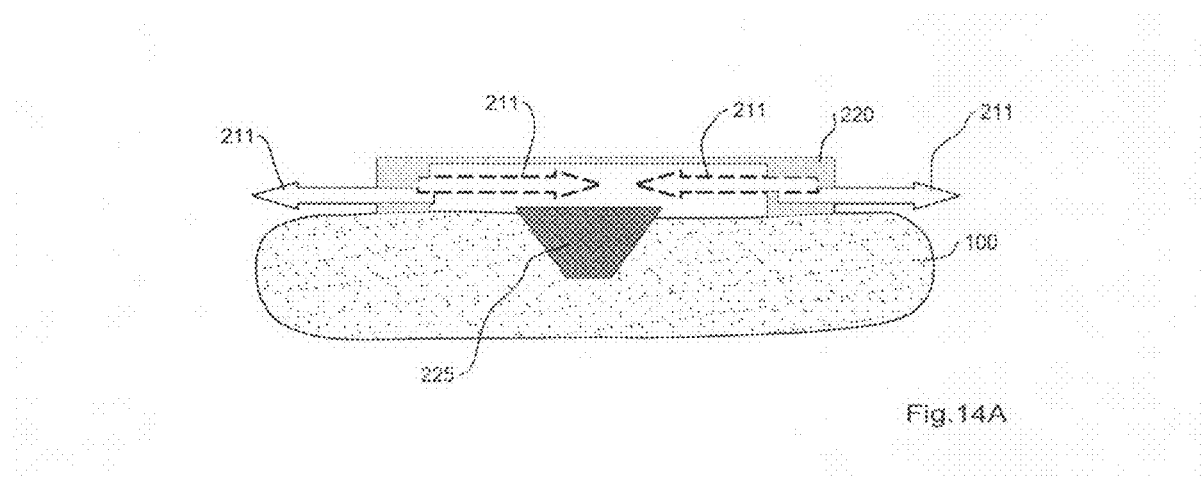
Fig.14A
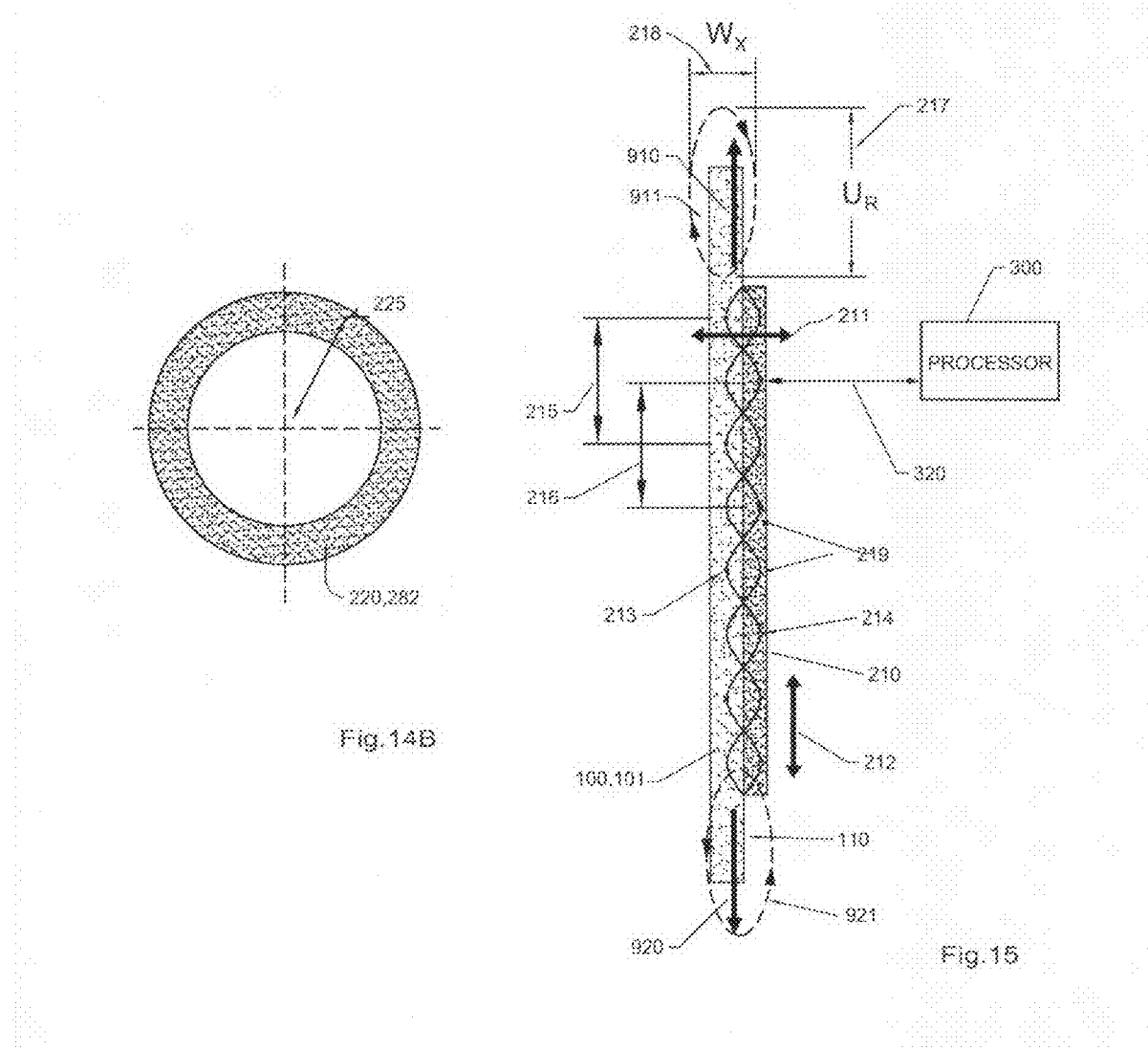
Fig.14B
Fig.15

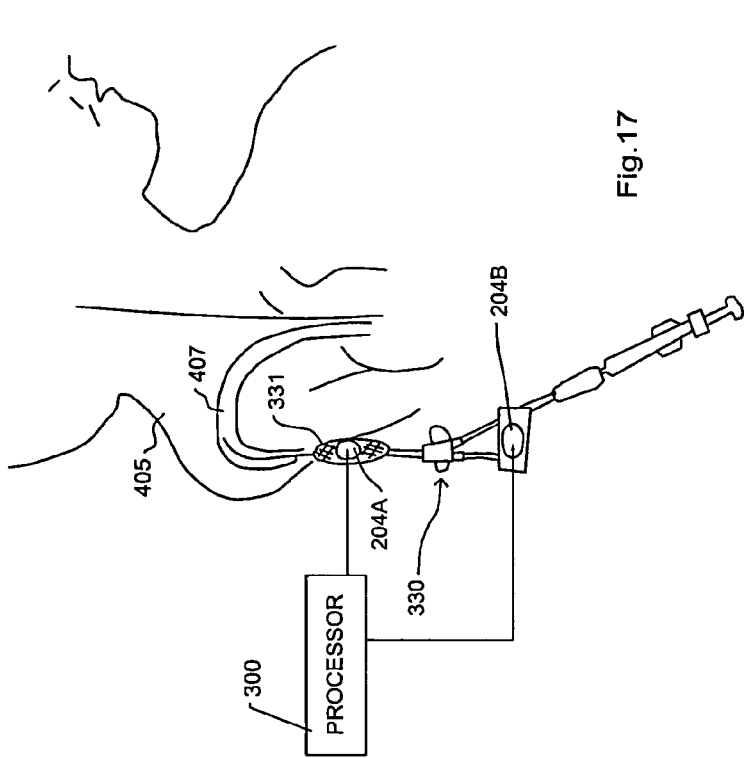
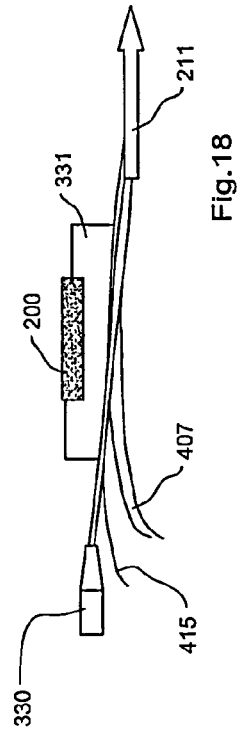
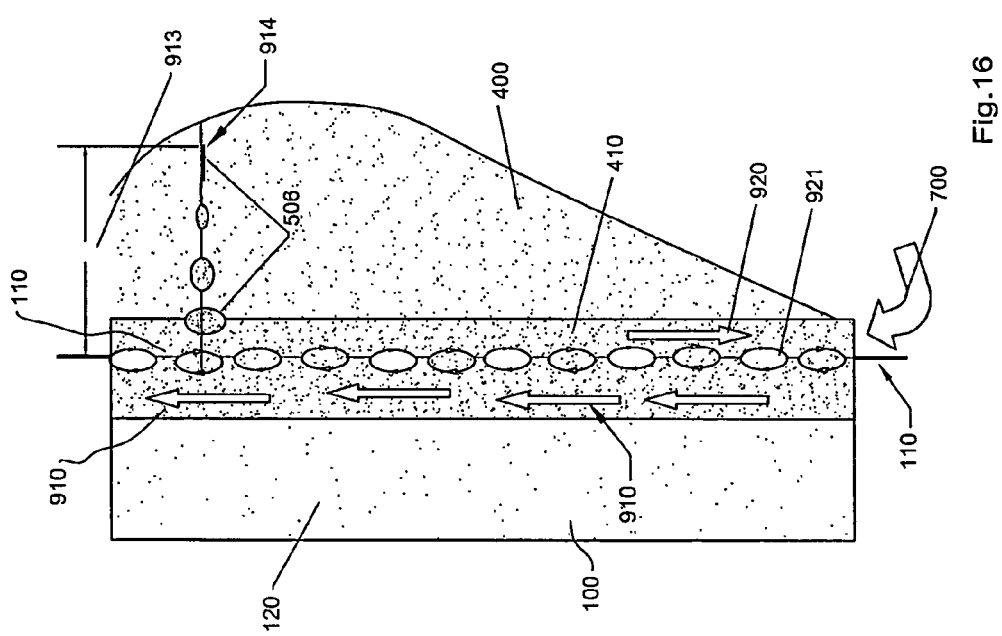

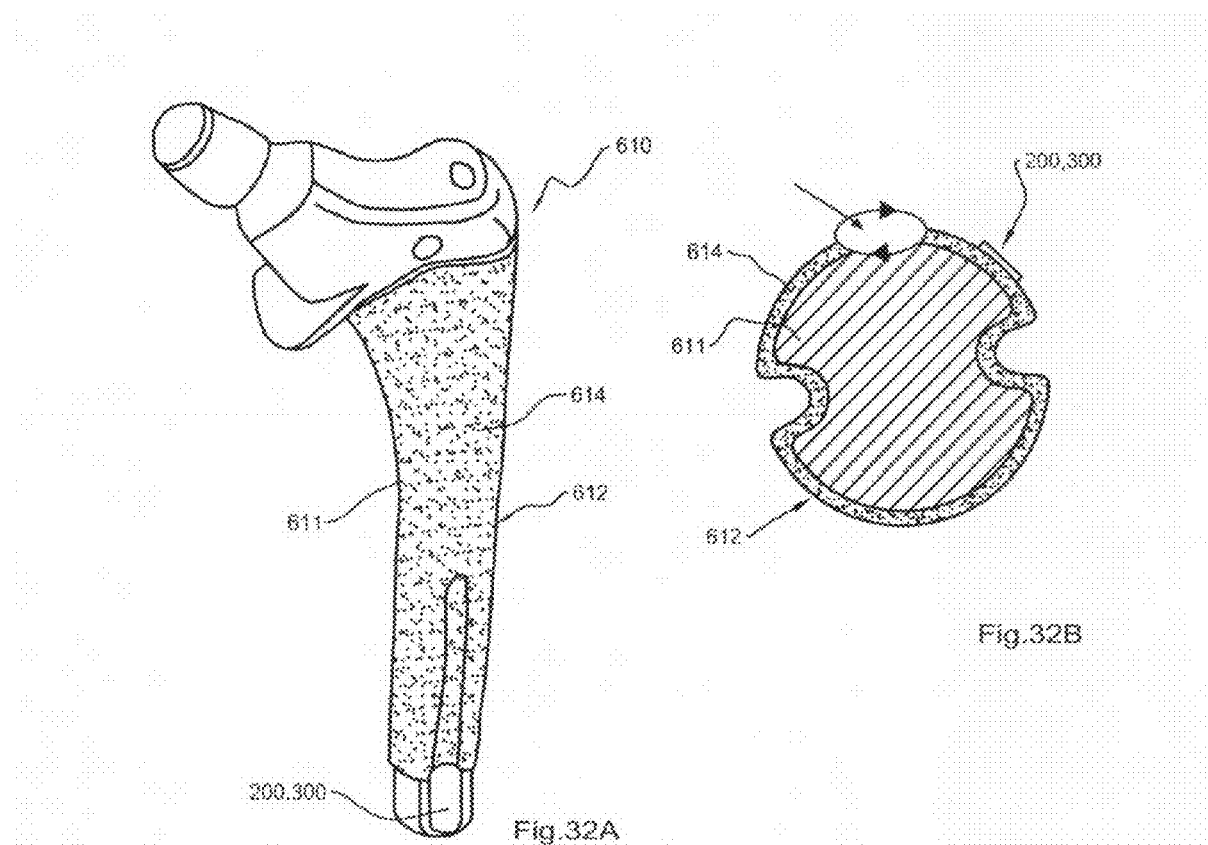
Fig.32A
Fig.32B
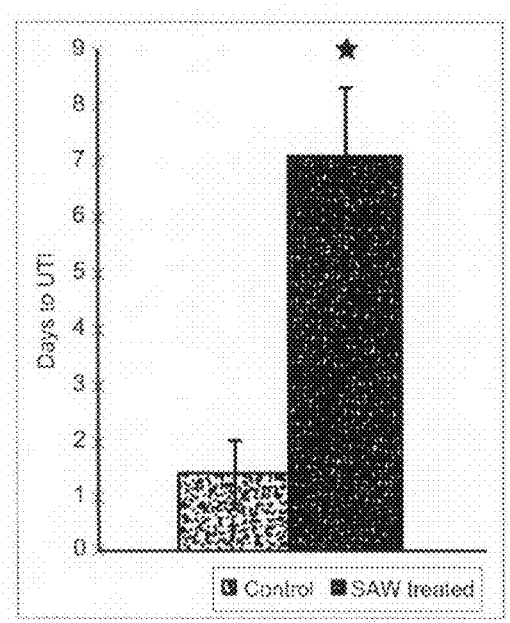
Fig.34 a. Treated Group b. Control

SYSTEM AND METHOD FOR SURFACE ACOUSTIC WAVE TREATMENT OF MEDICAL DEVICES

CROSS REFERENCE TO RELATED APPLICATIONS

This application claims the benefit of U.S. Provisional Application Ser. No. 60/776,067, filed on Feb. 24, 2006, which is incorporated in its entirety herein by reference.

FIELD OF THE INVENTION

The present invention relates to methods for producing surface acoustic waves on surfaces of medical devices.

BACKGROUND OF THE INVENTION

Indwelling device-related infections constitute a major cause of morbidity and mortality in hospitalized patients and add considerably to medical cost. Microbial biofilms tend to readily develop on all types of devices: urinary, endotracheal, intravenous and other types of catheters and implants inserted into more than 25% of patients during hospitalization. A variety of methods have been used to combat surface colonization of biomedical implants by bacteria and other microorganisms as well as the resulting biofilm formed. Previous methods have included varying the fundamental biomaterial used in the devices, applying hydrophilic, hydrophobic or bioactive coatings or creating porous or gel surfaces on the devices that contain bioactive agents. Antimicrobial agents, such as antibiotics and polyclonal antibodies integrated into porous biomaterials have been shown to actively prevent microbial adhesion at the implant site. However, the effectiveness of such local-release therapies is often compromised by the increasing resistance of bacteria to antibiotic therapy and the specificity associated with antibodies. Mechanical approaches to preventing biofilm formation have utilized ultrasonic energy, yet the focus has thus far been on increasing biofilm sensitivity to antibiotics. Ultrasound combinations with antibiotics were found effective only in reducing $E.\ coli$ biofilm burden in animal models, falling short of providing a comprehensive solution to the biofilm problem.

In addition, it is technically difficult to power such treatment systems, particularly for devices which are implanted in the body, and also to adequately spread the treatment over various shapes and configurations of devices.

SUMMARY OF THE INVENTION

According to embodiments of the present invention, there is provided a method for treatment of a surface of a medical device. The method includes providing an actuator for producing surface acoustic waves on a surface of the medical device and a processor for controlling parameters of the actuator, producing elliptical motion of particles on the surface of the medical device by activating the actuator and thereby producing the surface acoustic waves, wherein the elliptical motion causes relative bacteria vibration at a particular vibration amplitude, and controlling parameters of the actuator via the processor such that the vibration amplitude of the bacteria is smaller than a Z-potential repulsive zone of the bacteria.

According to further aspects of the present invention, there is provided a system for implantation in a body. The system includes an implantable device comprised of piezoelectric material and a processor for providing electrical signals to the piezoelectric material, the electrical signals configured to create surface acoustic waves by a direct piezoelectric effect on the implantable device, and the processor further configured to receive electrical signals from the piezoelectric material by a reverse piezoelectric effect, the received electrical signals proportional to the created mechanical vibrations.

According to further aspects of the present invention, there is provided a method for providing surface acoustic waves to a medical device. The method includes providing a medical device, an actuator positioned on the medical device, and a processor in electrical communication with the actuator, positioning the medical device in a body, powering the processor through body movements, and activating the actuator by the powered processor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which:

FIG. 14A is an illustration of creation of surface acoustic focused standing waves using a ring-shaped piezo-element;

FIG. 14B is an illustration of a ring-shaped piezo-element;

FIG. 15 is a schematic illustration of surface acoustic wave generation on a device, generating elliptical motion on the device;

FIG. 16 is a schematic illustration of a device positioned next to a body tissue, and depicting surface acoustic waves in motion and its effect at different depths within the tissue;

FIG. 17 is an illustration of a central venous catheter system inserted into a body of a patient;

FIG. 18 is an illustration of an enlarged pad from the catheter system of FIG. 17;

FIGS. 32A and 32B are illustrations of an orthopedic implant in the form of a hip stem, having a substrate and a porous layer;

FIG. 34 is a graphical illustration showing the average number of days to development of urinary tract infection with and without treatment.

Figure 1:
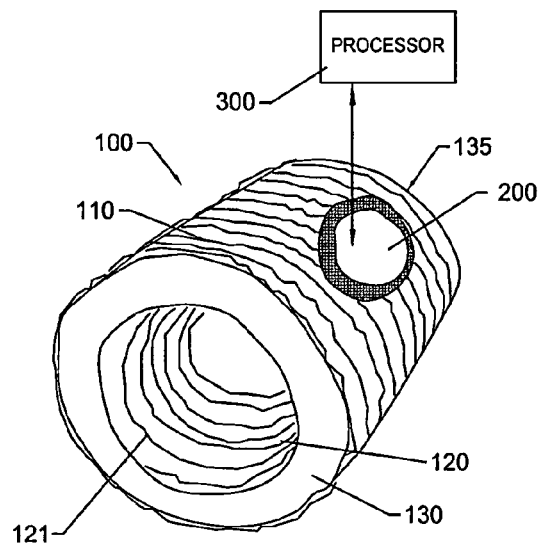
FIG. 1 is a schematic illustration of a medical device with an actuator for producing surface acoustic waves, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to methods for treating the surfaces of medical devices with surface acoustic waves. Specifically, the present invention can be used to treat biofilms that form on implantable medical devices by disrupting bacterial growth via surface acoustic waves (SAW) having frequencies on a nanoscale. The principles and steps of methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

1. Basic Principles

Reference is now made to FIG. 1, which is a schematic illustration of a medical device 100 with an actuator 200 for producing surface acoustic waves, in accordance with embodiments of the present invention. Device 100 has an external surface 110, an internal surface 120 a first end 130 and a second end 135. An actuator 200 is attached to external surface 110. Actuator 200 in electrical communication with a processor 300. Processor 300 may be, for example, a central processing unit (CPU), and may include an oscillator, an amplifier, and any other component used for receiving and transmitting signals and making calculations related to the received and transmitted signals. Upon receipt of an electrical signal from processor 300, actuator 200 is capable of generating high frequency mechanical vibrations, in a range from KHz to MHz. These high frequency mechanical vibrations create surface acoustic waves 121 (in the nanometer range) on internal surface 120 and external surface 110 of device 100. The frequency of generated mechanical oscillations in actuator 200 is directly related to the frequency produced by processor 300. Thus, for example, if oscillations are in the MHz range, the mechanical vibrations will also be in the MHz range, and similarly for other ranges. The energy source applied via processor 300 may have a periodical or non-periodical character, and may be electro-mechanical, electro-magnetic, or electro-optical.

Actuator 200 may be comprised of one or multiple piezo-electric transducers, one or more electromagnetic acoustic transducers, or one or multiple laser pulse transducers. In the case of piezoelectric and electromagnetic transducers, direct contact between actuator 200 and device 100 is necessary. In the case of laser pulse transducers, non-contact methods may be employed.

The term "surface acoustic waves" or "SAW" as used throughout the present disclosure, includes several types of waves or combinations thereof, as follows:

Surface—Rayleigh (elliptical orbit—symmetrical mode)
Plate Wave—Lamb—component perpendicular to surface (extensional wave)
Plate Wave—Love—parallel to plane layer, perpendicular to wave direction
Stoneley (Leaky Rayleigh Waves)—wave guided along interface
Sezawa—antisymmetric mode Surface or Rayleigh waves travel along the boundary between two different media, penetrating to a depth of about one wavelength. The particle movement has an elliptical orbit. Lamb wave is a special case of Rayleigh waves, which occurs when the material is relatively thin.

Attraction or repulsion of bacteria is an outcome of Van der Waals and hydrophobic attraction forces being counteracted by electrostatic repulsion in the 10 nm range near the surface—a phenomenon known as Z potential. SAW induce elliptical vibrations, and the amplitude at which the bacteria vibrate is smaller than that of the surface vibrations. The result is a relative velocity of bacteria respective to the surface.

When the SAW-generated bacterial vibration amplitudes are smaller than the Z potential repulsive zone, an overall net repulsion occurs, preventing bacterial attachment, and being effective in: inhibiting particle attachment to the surfaces, inhibiting adhesion, growth and aggregation of cells into micro colonies process on the surfaces, maturation and dissemination of progeny cells for new colony formation.

Increasing the bacteria vibration amplitudes to values exceeding the Z potential repulsion zone will result in a net attraction force, promoting the adhesion of bacteria. For this reason, many regimes which seek to use ultrasound energy to disrupt bacterial adhesion fail, since the vibration amplitudes are too high.

Figure 2:
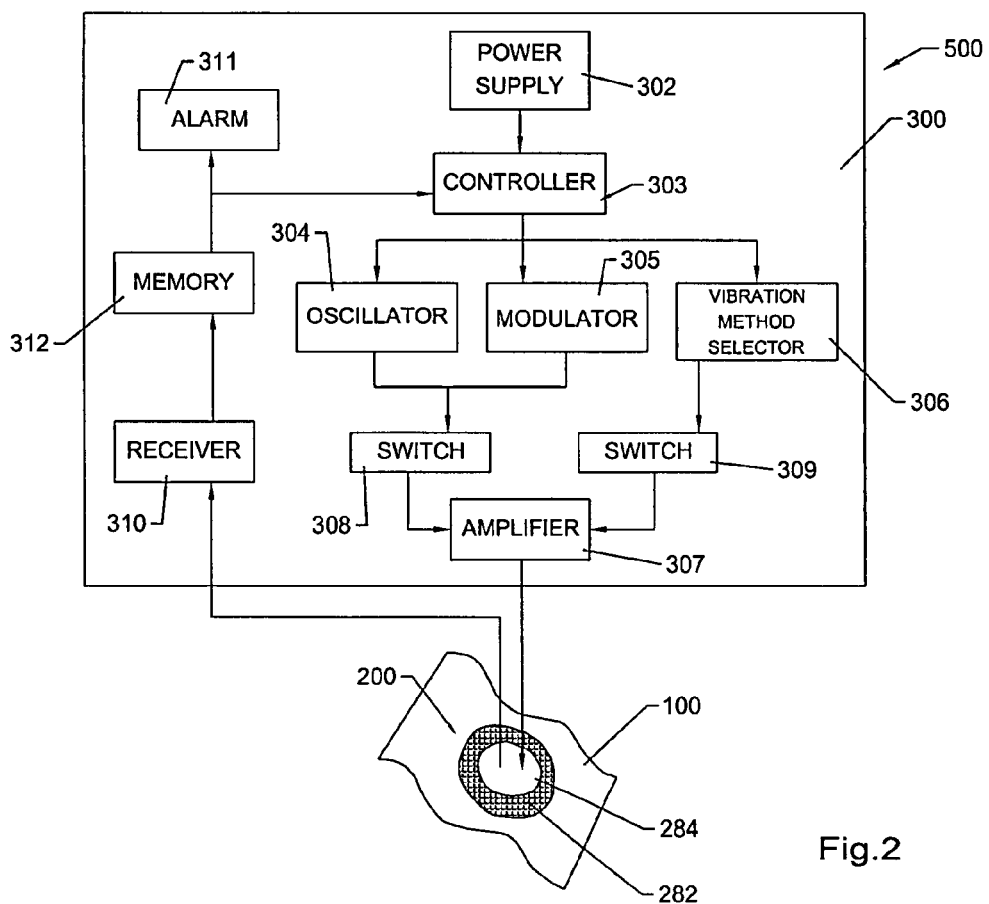
FIG. 2 is a block diagram illustration of a system for treating a medical device using surface acoustic waves, in accordance with embodiments of the present invention.

Reference is now made to FIG. 2, which is a block diagram illustration of a system 500 for treating a medical device using SAW, in accordance with embodiments of the present invention. The system shown herein is useful in creating SAW via a piezoelectric actuator. However, as noted below, other methods may be used to create SAW as well, including electromagnetic stimulation and laser pulse excitation. System 500 includes an actuator 200 having an activating portion 282 and an electrode portion 284, a processor 300 in electrical communication with electrode portion 284 of actuator 200, and optionally a matching layer positioned between actuator 200 and a device 100. In the embodiment shown herein, actuator 200 a piezoelectric actuator, and works by converting electrical signals from processor 300 into mechanical energy, wherein the mechanical energy is transmitted to device 100 and creates SAW on surfaces thereof. In some embodiments, actuator 200 is configured to transmit electrical signals proportional to the mechanical energy created to processor 300, and may thus provide a feedback loop to regulate the electrical signals produced by processor 300. The matching layer may optionally be placed between actuator 200 and device 100 in order to match acoustic signal transmission properties of materials used to construct device 100 and actuator 200.

Processor 300 includes a power supply 302 for providing electrical energy to system 500. In some embodiments, power supply 302 is a separate unit (such as a power cord), and in some embodiments, power supply 302 is incorporated into processor 300 (such as a battery). Processor 300 further includes a controller 303 for controlling output parameters of processor 300. Controller 303 is in electrical communication with an oscillator 304 for providing signals at various frequencies, a modulator 305 for modulating parameters such as frequency, amplitude, etc., and a vibration method selector 306 for providing different types of vibrations, such as single-phase, two-phase or multi-phase vibrations. Oscillator 304 and modulator 305 are connected to a first switch 308, for selection of signal parameters. Vibration method selector 306 is connected to a second switch 309 for selection of vibration method. The selected signal of the selected vibration type is sent through an amplifier 307 to actuator 200.

For embodiments wherein electrical signals are sent from actuator 200 to processor 300, these signals are received by a receiver 310 within processor 300. It should be noted that in some instances, signals are sent by a separate sensor placed on or near or incorporated within actuator 200, as will be described in further detail hereinbelow. Signals received by receiver 310 are sent to a memory module 312, where they are compared with expected values. Results of the comparison are then either sent to controller 303, where signal parameters such as amplitude and frequency may be automatically adjusted based on the received information, or sent to an alarm 311 for alerting a user that parameters should be adjusted manually.

Selection of parameters depends on the use and application of system 500, and may vary according to specific requirements. For example, use of a urinary catheter as an indwelling device includes three phases—an insertion phase, an indwelling phase and a removal phase. The indwelling phase may last up to 30 days and may itself include separate healing phases. Each of these phases may have different requirements, leading to selection of different parameters. During the insertion phase for example, a two-phase electrode method may be chosen, wherein two electrodes working together produce larger vibration amplitudes. This type of effect is desirable, for example, during insertion of a catheter, when friction reduction is desired. During an indwelling phase, at different points in time, different frequencies and/or amplitudes may be chosen, depending on the stage of healing. For example, modulator 305 may modulate a MHz signal with a KHz signal by additive synthesis, and a single-phase vibration may be chosen, because although friction reduction is not important during this phase, relative velocity of bacteria for reduction of bacterial adhesion is important during this phase. This result may be achieved with smaller amplitudes, such as those obtained via a single-phase vibration scheme. These parameters allow a decrease of energy requirements for inhibiting biofilm and creating relative velocity of bacteria. During the removal phase, high amplitudes are desirable so that tissue trauma can be avoided. Thus, modulator 305 may modulate a KHz signal with a Hz signal and use a multi-phase vibration method.

Figure 3A:
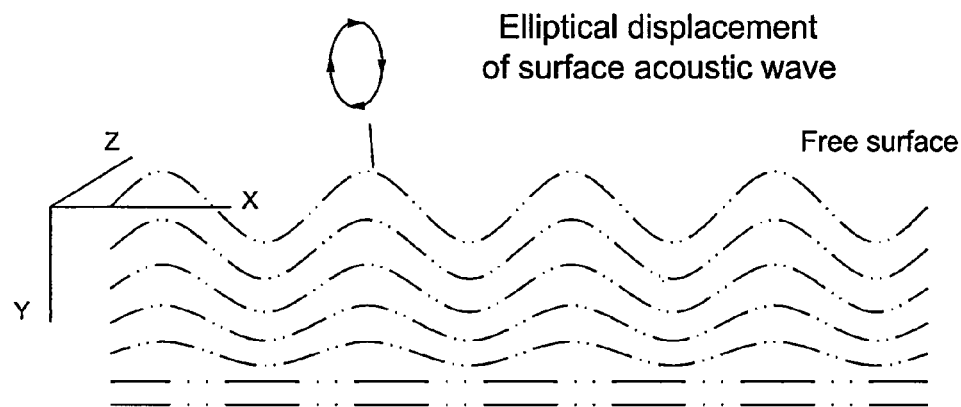
FIG. 3A is a schematic representation showing the propagation of a Rayleigh wave on an elastic surface.

Reference is now made to FIG. 3A, which is a schematic representation (not to scale) showing the propagation of a Rayleigh wave on an elastic surface. As shown in FIG. 3A, the physical motion of this "true-SAW" wave type is associated with mechanically time-dependent elliptical displacement of the surface structure. One component of the physical displacement is parallel to the SAW propagation axis X, and another component is normal to the surface along axis Y.

In general, the amplitude of surface displacement along the y-axis is larger than along the SAW propagation axis X. The amplitudes of both SAW displacement components are negligible for penetration depths (into the body of the solid, such as, for example device 100) greater than a few acoustic wavelengths.

Propagation of Lamb waves depends on density, elastic, and other material properties of the solid (such as device 100, for example), and they are influenced a great deal by selected frequency and material thickness. With Lamb waves, a number of modes of particle vibration are possible, but the two most common are symmetrical and antisymmetrical. The complex motion of the particles is similar to the elliptical orbits for surface waves.

Figure 3B:
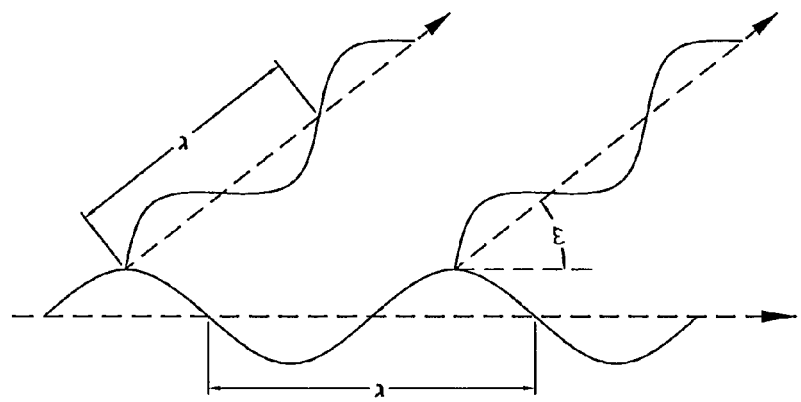
FIG. 3B is a schematic illustration showing the generation of a compressional wave into fluid by a surface acoustic wave having a wavelength $\lambda$ and delivered at an angle $\xi$ to an external surface of a device.

Reference is now made to FIG. 3B, which is a schematic illustration showing the generation of a compressional wave into fluid $\lambda_1$ by a SAW having a wavelength $\lambda$ and delivered at an angle $\xi$ to external surface 110 of device 100. Pressure (gas or fluid loading) also contributes to acoustic wave attenuation and velocity change. In this case, attenuation is due to the generation of compressional waves in the gas or fluid in contact with a surface of device 100. Thus, the shear vertical component of the wave causes periodic compression and rarefaction of the gas or fluid, resulting in a coupling of acoustic energy from device 100 into the gas or fluid. The condition for this to occur is:

$$\cos \text{angle } \xi = \lambda/\lambda_1$$

The presence of SAW on internal and external surfaces 120 and 110 of device 100 causes a pushing/pulling effect of materials on these surfaces, including fluids and particulates suspended therein. Thus, in the case of formation of a biofilm, the SAW may reduce the existing biofilm, augment and enhance the effect of antibiotics on the biofilm (i.e. decrease the biofilm's resistance to antibiotics), produce antimicrobial and antithrombogenic surfaces, and augment tissue therapy.

There are several methods for producing SAW on medical devices, including electromagnetic, laser pulses, or piezo-electric methods, as will be discussed in greater detail hereinbelow.

Electromagnetic Transducers

Figure 4:
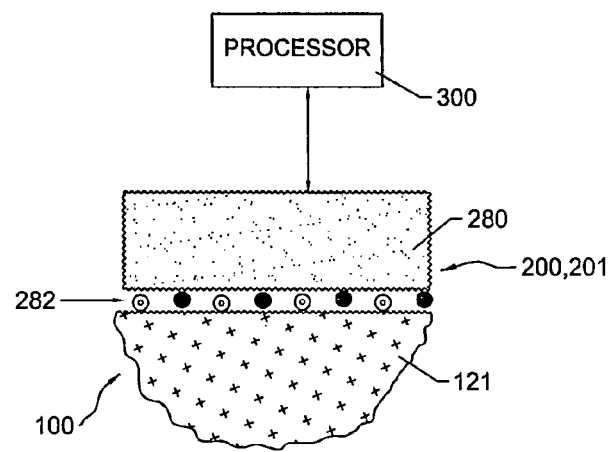
FIG. 4 is a cross-sectional illustration of a device with an actuator attached thereto, wherein the actuator is comprised of an electromagnetic transducer.

Reference is now made to FIG. 4, which is a cross-sectional illustration of a device 100 with an actuator 200 attached thereto, wherein actuator 200 is comprised of an electromagnetic transducer 201. As shown in FIG. 4, actuator 200 is comprised of a base portion 280 and an activating portion 282. Base portion 280 may be of any conductive material, such as a metal and activating portion 282 is comprised of electromagnetic transducers, such as electromagnetic ultrasound transducers available from Olympus company, Panametrics-NDT Ultrasonic Transducer. SAW in the desired range may be obtained by varying the frequency of the electromagnetic transducer. Activating portion 282 is configured to excite Lamb waves in plates. This type of actuator vibrates the atoms within device 100. Processor 300 is in electrical communication with base portion 280. Processor 300 applies a current to base portion 280, which comprised of an electrically conductive material. When the current is applied at a particular ultrasonic frequency, electromagnetic transducers (activating portion 282) create vibrations of Lamb wave type, wherein the distance between maximum amplitudes will be equal to one-half the wavelength of SAW excited on device 100.

Pulsed Laser Transducers

Figure 5:
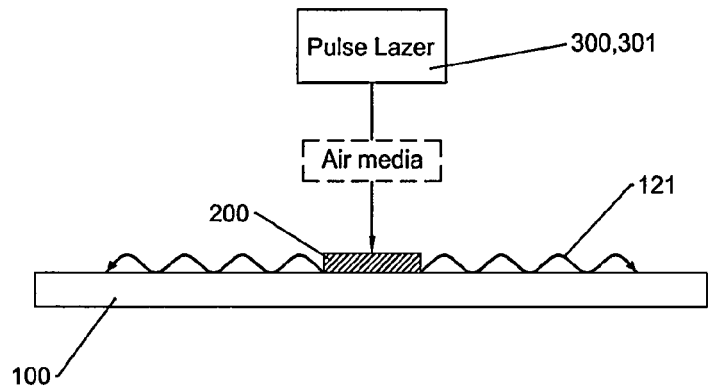
FIG. 5 is a diagrammatic illustration of a device with a processor, wherein the processor is a pulsed laser device.

Reference is now made to FIG. 5, which is a diagrammatic illustration of a device 100 with a processor 300, wherein processor 300 is a pulsed laser device 301. Actuator 200 is a metallic plate which is configured to vibrate in response to laser pulses from processor 300. No contact is necessary between actuator 200 and processor 200 since laser pulses travel through the air. Pulsed laser device 301 is used to generate SAW 121 in solids by a thermoelastic mechanism, wherein the resulting elastic displacement waveform has a wide band. The frequency range of the SAW excited using pulsed lasers has limited bandwidth as only short pulse widths may be excited with pulsed laser device 301 in a solid. The amplitude and frequency bandwidth of the laser-induced SAW are improved by decreasing the radius of the focused laser spot. For example, laser pulse focused to a line produced by Max-Planck-Institute for Solid State Research may be applied.

Piezo-Electric Transducers

Actuator 200 may include one or more piezo-actuators 203, which are configured to provide SAW in accordance with embodiments of the present invention. These piezo-actuators 203 are configured to provide vibrations at amplitudes of between 0.2-2 nanometers.

Figure 6A:
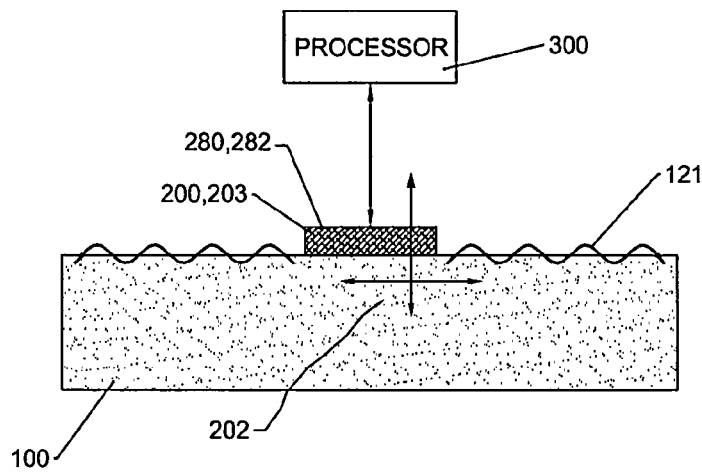
FIG. 6A is an illustration of an actuator having a base portion comprised of a piezo-element, wherein the base portion acts as an activating portion.
Figure 6B:
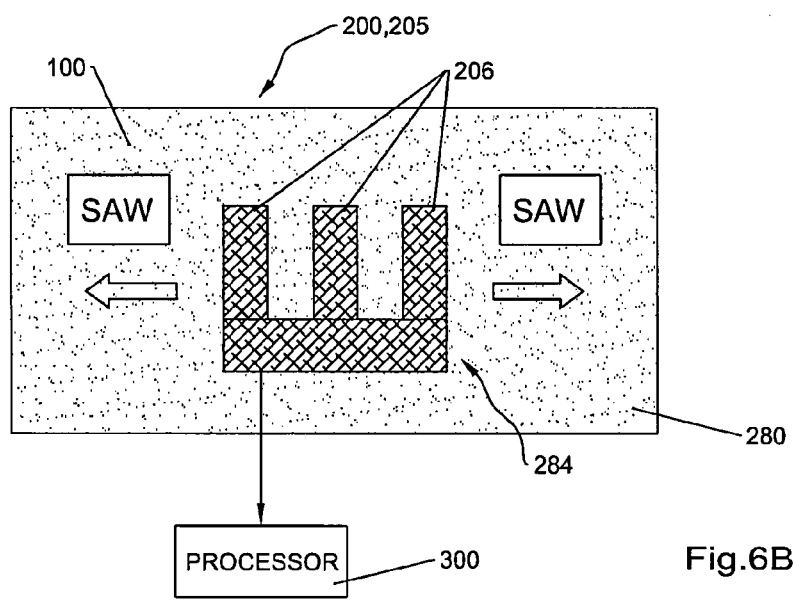
FIG. 6B is an illustration of an actuator which is an IDT actuator.
Figure 6C:
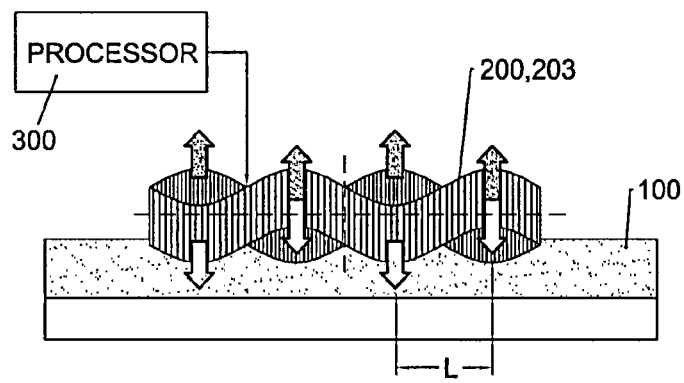
FIG. 6C is an illustration of the actuator of FIG. 6A, during vibrations.

Reference is now made to FIGS. 6A-6C, which are illustrations of actuator 200, wherein actuator 200 is comprised of one or multiple piezo-elements 203. Actuator 200 may include a base portion 280 and an activating portion 282, wherein activating portion 282 is comprised of piezo-elements 203. It should be noted that electrodes must be included on piezo-elements 203. In many of the figures, these electrodes are not shown since the different possibilities for positioning of electrodes are known to those skilled in the art. In some embodiments, base portion 280 is also the activating portion 282 and is thus comprised of piezo-elements 203. As shown in FIG. 6A, actuator 200 is comprised of a base portion 280, wherein base portion 280 is a piezo-element 203, and thus acts as an activating portion 282. In some embodiments, multiple piezo-elements 203 are used. Actuator 200 may work in thickness and/or radial vibration modes thus generating SAW 121 on surfaces of device 100. Vibrations of piezo-element 203 should occur in two planes, as depicted by arrows 202.

In the embodiment shown in FIG. 6B, actuator 200 is an integrated piezo-transducer, also known as an interdigital transducer (IDT) 205, having multiple elongated portions 206 or fingers, generating SAW on surfaces of device 100 when the distance L between two of elongated portions 206 is proportional to one-half [*that is the proper way to say it] the length of the SAW.

The IDT 205 comprises a base portion 280 which also may act as activating portion 282. Activating portion 282 includes a piezoelectric material with an electrode portion 284 sprayed thereon in a particular configuration such as the one shown in FIG. 6B. It should be noted that the configuration shown in FIG. 6B represents three different possible setups for IDT 205. In one embodiment, base portion 280 is comprised of a piezoelectric material and acts as activating portion 282, with electrode portion 284 sprayed thereon in a "comb" configuration as shown or in any known configuration for IDT. In another embodiment, base portion 280 is comprised of a material which is not piezoelectric, and activating portion 282 and electrode portion 284 are both configured in a "comb" configuration as shown or in any known configuration for IDT. That is, the shape of the piezoelectric material matches the shape of the electrode. In a third embodiment, activating portion 282 and electrode portion 284 are both configured in a "comb" configuration as shown or in any known configuration for IDT and are placed directly on device 100. Thus, actuator 200 includes an activating portion 282 and electrode portion 284 both of which have a particular configuration suitable for use as an IDT. Electrode portion 284 faces away from device 100, and base portion 280 and/or activating portion 282 is coupled to device 100—either directly or with the use of a matching layer. In all of the above described configurations, electrode portion 284 is in electrical communication with processor 300. When a voltage is applied to electrode portion 284 via processor 300, then a thickness vibration is initiated in activating portion 282 and Lamb waves are initiated by a resonance effect. The energy distribution from the vibrating elements is in two opposite directions. The distance between elongated elements L is equal to half the wavelength of SAW which is excited with this method. Most electrode configurations concentrate the created energy in the surface layer up to 100μ. The number of electrode elements 206 can vary depending on the desired amplitude of the SAW. The IDT transducer elongated elements may be excited with magnetic or laser means, too.

Many other configurations for electrode portion 284 are possible, and are known in the art. For example, two electrode portions may be positioned facing each other such that elongated portions of one interlock with elongated portions of the other, with gaps therebetween. The electrical voltage is applied to both electrode portions and the direction of SAW propagation is in two directions. In some embodiments, a continuous electrode may be used. The distance between the elongated portions is equal to $\lambda_a$, i.e. the wave transits the distance between each pair of electrode elements precisely by the time equal to the phase of the exciting signal. Therefore the SAW intensity is proportional to the number of pairs of electrode elements. In another embodiment, electrode portion 284 includes two external active electrodes and multiple passive electrodes positioned between the active electrodes. By varying the number of passive electrodes it is possible to change the width of the range of frequencies to change resistance of radiation $N^2/4$ times, where N is the number of passive electrodes.

Reference is now made to FIG. 6C, which is an illustration of an actuator 200 such as the actuator shown in FIG. 6A, during vibrations. Actuator 200, after activation by processor 300, begins to vibrate in two directions—up and down—as shown by gray and white arrows, respectively. Vibrations of piezo-element 203 generate SAW on the internal surface 120 and external surface 110 of device 100 when a distance L between two maximal amplitudes of bending vibration modes are proportional to one-half the length L of the SAW. In this embodiment, piezo-element 204 is configured to work with symmetrical Lamb vibration modes. This method works similar to the IDT 205. The standing wave maximal amplitudes created in a thin plate are similar to elongated portions 206 of IDT 205, creating elastic deformations in the material of device 100 and exciting SAW thereon. In some embodiments, a matching layer may be positioned between actuator 200 and device 100. For example, a glue layer for attaching actuator 200 to device 100 may be used, wherein the glue layer has a smaller acoustic velocity than piezo-element 203 but a larger acoustic velocity than the material of device 100.

Figure 7:
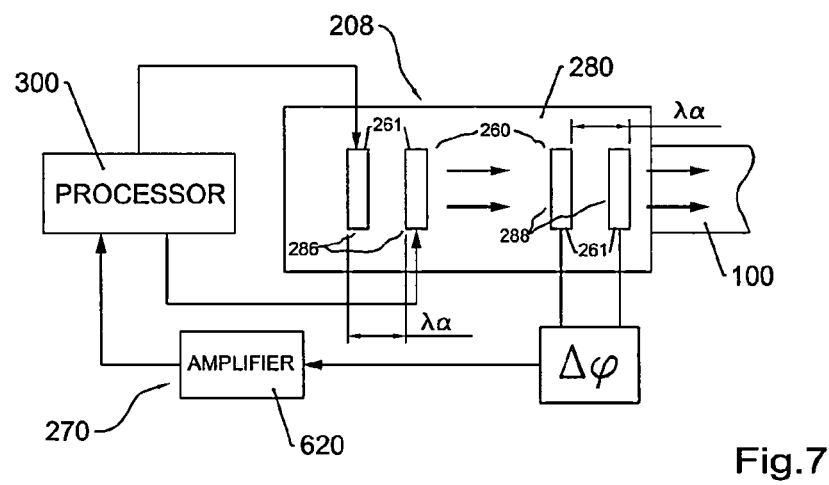
FIG. 7 is an illustration of an electrode actuator, further incorporating an acoustic feedback and monitoring system.

Reference is now made to FIG. 7, which is an illustration of an electrode actuator 208, further incorporating an acoustic feedback and monitoring system 270. Electrode actuator 208 is comprised of a base portion 280 and an electrode portion 260. Base portion 280 is a piezo-electric plate, and electrode portion 260 includes multiple electrode elements 261 sprayed onto base portion 280. In the embodiment shown herein, multiple electrode elements 261 are grouped into two pairs. A first pair acts as an excitation pair 286, and a second pair acts as a sensing pair 288. A distance between electrode elements 261 of each pair is equal to the length of SAW $\lambda_a$ in the acoustic line. Excitation pair 286 is in electrical communication with processor 300. Processor 300 provides a current to excitation pair 286, thus producing SAW through base portion 280, wherein the SAW have wavelengths of $\lambda_a$. The amplitudes of excited SAW depend on the current range. Sensing pair 288 senses a signal obtained due to the piezo-electric effect of base portion 280. The shift of the signals Δφ is amplified via an amplifier 620, and the amplified signal is sent to processor 300. This signal is used to provide feedback and may be used to change the parameters of the output of processor 300. For example, if the frequency does not produce expected vibrations (due to variations in geometry, for example), the voltage supplied to excitation pair 286 can be changed. The construction supposes some acoustic energy scattering on base portion 280. In some embodiments, a surface of medical device 100 is comprised of piezo-electric material, and may act as base portion 280, eliminating the need for an additional plate.

Figure 8:
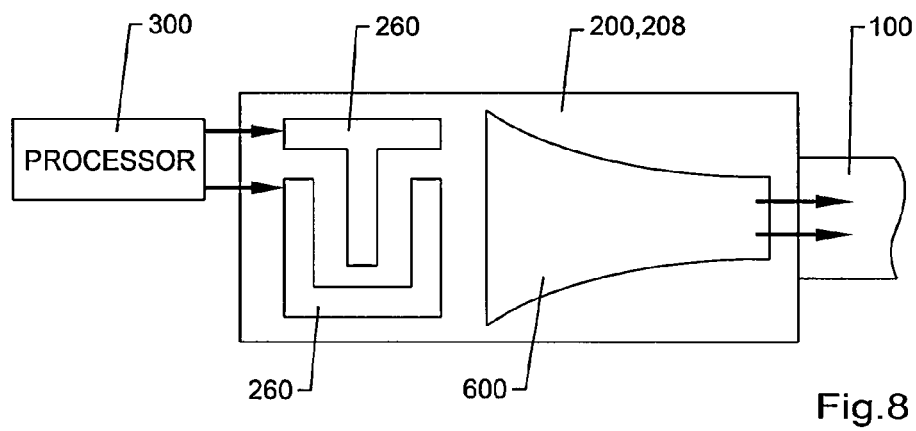
FIG. 8 is an illustration of an actuator constructed using a flat concentrator.

Reference is now made to FIG. 8, which is an illustration of an actuator 200 constructed using a flat concentrator 600. SAW amplitude may be increased when flat concentrators of elastic vibrations are applied. Such flat concentrators may vary in their form, and may have exponential, cones, Gaussian or other shapes. Concentrator 600 may be attached to actuator 200, or alternatively, a configuration of actuator 200 may be provided wherein a portion is shaped as desired in order to form a concentrating region. It is possible to enlarge or reduce SAW amplitude, if necessary. Using flat concentrators of elastic vibrations, matching between actuator 200 and device 100 may be achieved, for the different applications disclosed in the proposed invention.

Reference is now made to FIG. 9, which is a graphical illustration of a system 150 for producing an electric-acoustic effect, which is essentially an amplification of the acoustic effect. This amplification is sometimes necessary when an IDT is used, since the IDT generally does not provide a strong enough acoustic effect to create SAW of desired frequency and/or amplitude. The electric-acoustic effect occurs when ultrasonic waves of 10 MHz frequency and above interact with conducting electrons in metals and semiconductors. When acoustic-electronic interaction has taken place, there is an interchange of energy between an acoustic wave and conducting electrons. Piezoelectric interaction arises in piezo-electric semiconductors (piezo electrones): cadmium sulfide (CdS), zinc sulfide (ZnS), indium antimonide (InSb), gallium arsenide (GaAs) and others and is caused by the fact that their deformation is accompanied by occurrence of an electric field and, conversely, the electric field causes a deformation of the crystal. The resultant force depends on electrical conduction of a piezo material and on the frequency of the acoustic wave.

When an acoustic wave spreads in a piezoelectric semiconductor, the transfer of acoustic wave impulse to electrons may occur, and a so-called acoustic-electric current is achieved. In a case when an additional exterior constant electric field E is applied to the same crystal, the field results in a drift of electrons in a direction of acoustic wave propagation. The resulting acoustic-electronic interaction depends on a relationship of charge carriers, drift velocity Vd, and sound velocity C. The velocity of SAW, as it is known, is much lower than the velocity of spherical waves.

Under certain conditions, when sound velocity is greater than velocity of electrons, electrons will transfer their kinetic energy to the acoustic wave. In this case the amplification of acoustic wave is observed. The amplification coefficient can reach tens of decibels. This effect is most favorable for SAW in the layer of $\lambda-2\lambda$ thickness and working in a traveling wave regime. Furthermore, the continuous amplification regime with high energy and reduced interferences may be achieved. The piezoelectric interaction usage may result in some non-linear acoustic effects and generation of acoustic wave harmonics. The presence of higher harmonics can yield a series of positive effects: in acoustics—a more uniform coat with oscillations, in biology—the action of ultrahigh frequencies (harmonics of a basic frequency) on biological objects (for example, on biofilms).

Figure 9A:
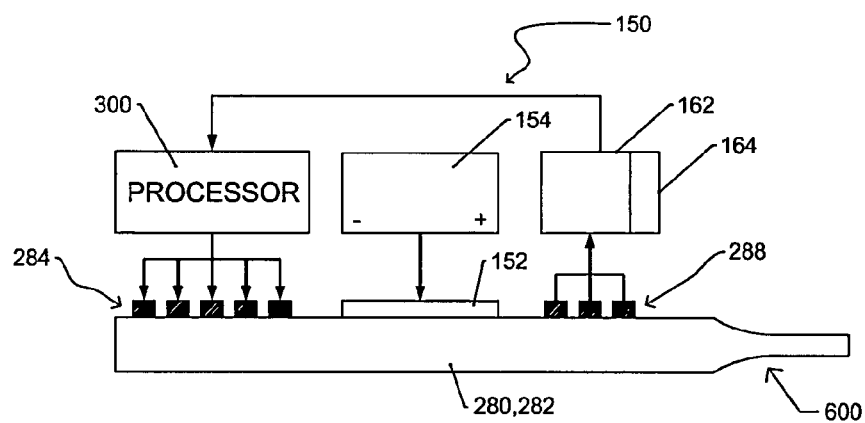
FIG. 9A is a graphical illustration of a system for producing an electric-acoustic effect.

As shown in FIG. 9A, a system 150 for producing an electric-acoustic effect includes an activating portion 282 (which is also a base portion 280), an electrode portion 284 wherein electrode portion 284 is sprayed onto base portion 280, a semiconductor plate 152 attached to activating portion 282, and optionally a sensor pair 288, also sprayed onto activating portion 282. Electrode portion 284 is activated via processor 300, and semiconductor plate 152 is activated by a power source 152 for DC current. In some embodiments, processor 300 and power source 152 are combined into one unit, and in other embodiments they are separate. At the site of contact between activating portion 282 and semiconductor plate 152, there is an interaction of acoustic wave SAW with directional electrons as they have the same direction. Thus, semiconductor plate 152 creates an electric-acoustic effect which amplifies the vibrations. The amplified SAW vibrations are further transmitted through a layer of the activating portion and are partially damped due to a damping coefficient of the material. In some embodiments, a concentrator 600 may be included at one end of activating portion 282.

A sensing pair 288 may be included as well, wherein a feedback signal is sent from sensing pair 288 to a visualization sensor 164 for providing data about the wave and amplifier 162. This feedback signal is then sent to processor 300, and may be used to control the signal parameters, such as vibration amplitude. These parameters may often need to be changed based on the geometry of device 100. As such, a feedback system such as the one described may be helpful in optimizing SAW for different devices.

Figure 9B:
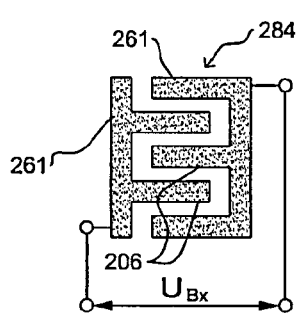
FIG. 9B is an illustration of a configuration of the electrode portion of the system of FIG. 9A.

Reference is now made to FIG. 9B, which is an illustration of a configuration of electrode portion 284, in accordance with embodiments of the present invention. Electrode portion 284 includes two electrode elements 261, each of which has elongated portions 206 which are interlocked with one another. Each of electrode elements 261 is in electrical communication with processor 300. It should be apparent that many other configurations of electrodes are possible as well.

Figure 9C:
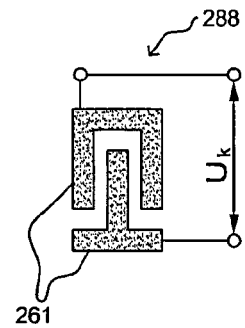
FIG. 9C is an illustration of a configuration of a sensor pair of the system of FIG. 9A.

Reference is now made to FIG. 9C, which is an illustration of a configuration of sensor pair 288, in accordance with embodiments of the present invention. Sensor pair 288 includes two electrode elements 261, each of which is in electrical communication with visualization sensor 164 and amplifier 162. It should be apparent that many other configurations of electrodes are possible as well.

Reference is now made to FIGS. 10A-10E, which are schematic illustrations of actuator 200 in accordance with several embodiments of the present invention. The actuators 200 depicted in FIGS. 10A-10E may differ from each other in a mode of spatially-non-uniform and variable elastic deformations, and in an aspect of energy parameters emitted on the medical devices. As shown in FIGS. 10A-10E, actuator 200 may have a "wedge" or "comb" type of configuration, wherein spherical waves (longitudinal and transverse) are transformed into surface waves.

Figure 10A:
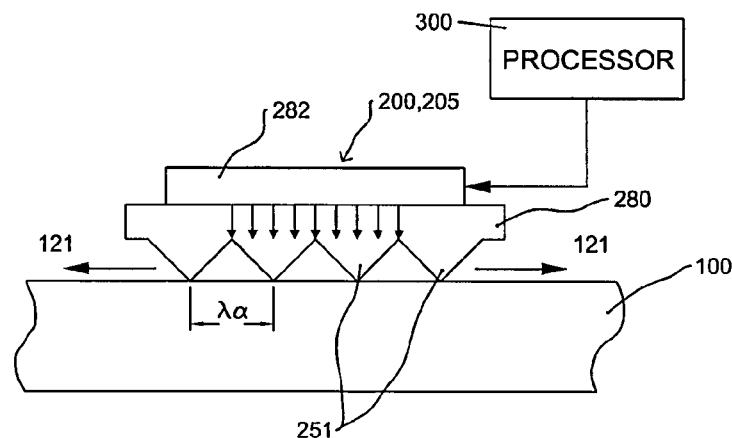
FIGS. 10A-10E are schematic illustrations of actuators in accordance with several embodiments of the present invention.

As shown in FIG. 10A, actuator 200 includes a base portion 280 and an activating portion 282. Base portion 280 comprises protruding elements 251 which are in contact with device 100. In the embodiment shown in FIG. 10A, each of protruding elements 251 has a triangular equilateral shape, and several of these protruding elements 251 are arranged in a row. Voltage is applied to activating portion 282 of actuator 200 via processor 300, which may include, for example, a power supply. Voltage from processor 300 excites elastic volumetric (three dimensional) vibrations in activating portion 282, which are transmitted to base portion 280 and to protruding elements 251. This results in production of SAW 121 in two opposite directions along device 100. It should be readily apparent that in some embodiments, base portion 280 is comprised of piezoelectric material and in other embodiments, only activating portion 282 is comprised of piezoelectric material. In some embodiments, when base portion 280 is comprised of piezoelectric material, base portion 280 acts as activating portion 282.

Figure 10C:
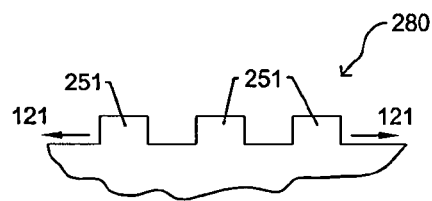
Figure 10B:
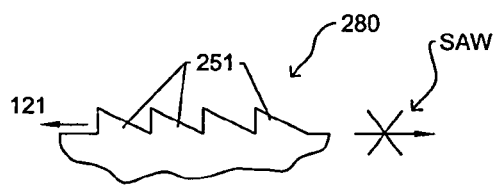

Reference is now made to FIG. 10B, which is an illustration of base portion 280 having protruding portions 251 which are rectangularly shaped. This configuration causes a two-directional vibration along one axis. The requirement of acoustic synchronization is ensured by means of distances between the grooves, which are equal to $\lambda_a$. Thus the SAW which spreads along the grooves excites a surface wave in device 100. Modification of the groove slope angle increases or decreases the vibration amplitude. As shown in FIG. 10C, protruding portions 251 may have an angled configuration such as a "comb" shape as well, enabling SAW propagation in one direction only.

Figure 10D:
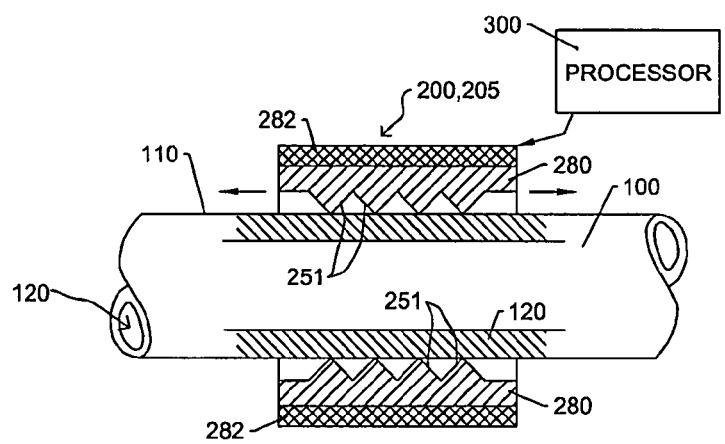
Figure 10E:
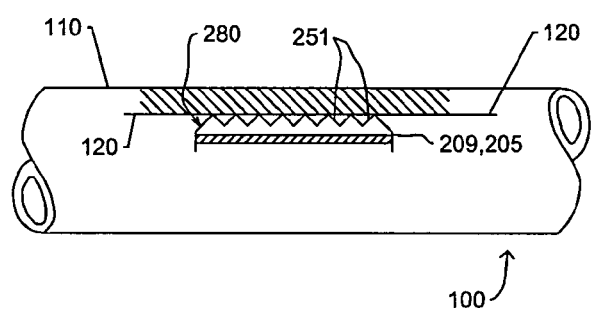

Reference is now made to FIGS. 10D and 10E, which are illustrations of a cylindrically shaped actuator 200 attached to a cylindrically-shaped device 100 and causing SAW excitement on external and internal surfaces 110 and 120 of device 100. Base portion 280 may have triangular equal-sided protruding elements 251, as shown in FIG. 10D or "comb" shaped protruding elements 251, shown in FIG. 10E. As shown in FIG. 10D, actuator 200 may be placed on an external surface 110 of device 100. Alternatively, as shown in FIG. 10E, actuator 200 may be placed on internal surface 120 of device 100.

Figure 11:
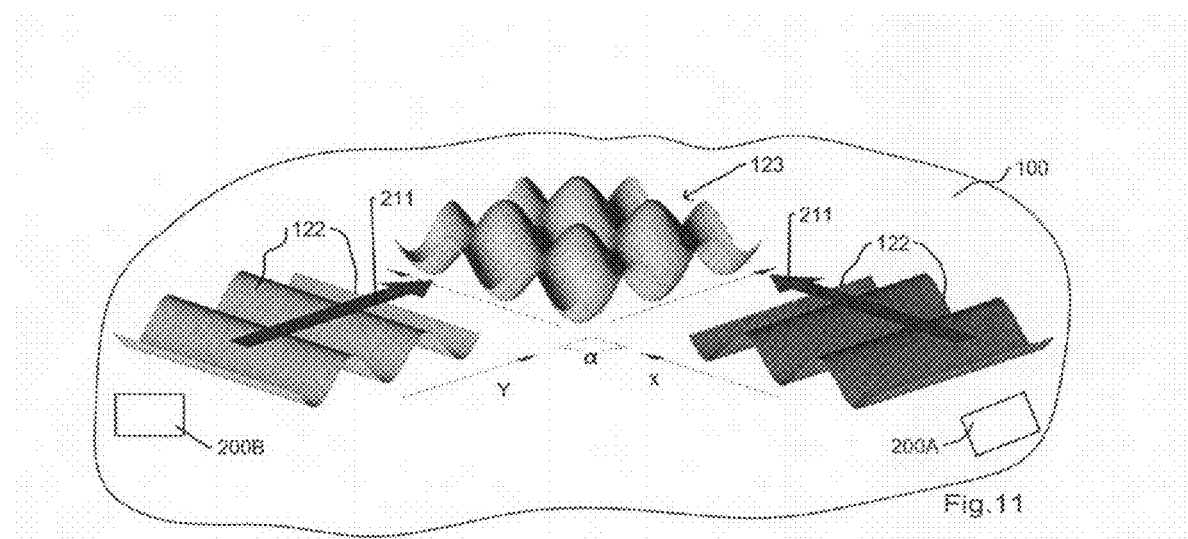
FIG. 11 is an illustration of a method for achieving surface acoustic waves, including a summation of surface acoustic waves from two actuators placed at an angle α relative to one another on a surface of a device.

Reference is now made to FIG. 11, which is an illustration of one method for achieving SAW, showing a summation of SAW from two actuators 200A and 200B placed at an angle α relative to one another on a surface of device 100. Thus, running type waves 122 excited and transmitted by each of actuators 200A and 200B (in directions indicated by arrows 211) interfere with each other, thus forming standing waves 123 on the surface of device 100. The waves' interferences in the areas of overlap concentrate acoustic energy. Thus, it is possible to create a concentrated SAW effect by strategic placement of actuators. In some embodiments, actuators 200A and 200B are connected to one processor 300. In other embodiments, separate processors may be used for each of actuators 200A and 200B.

Figure 12:
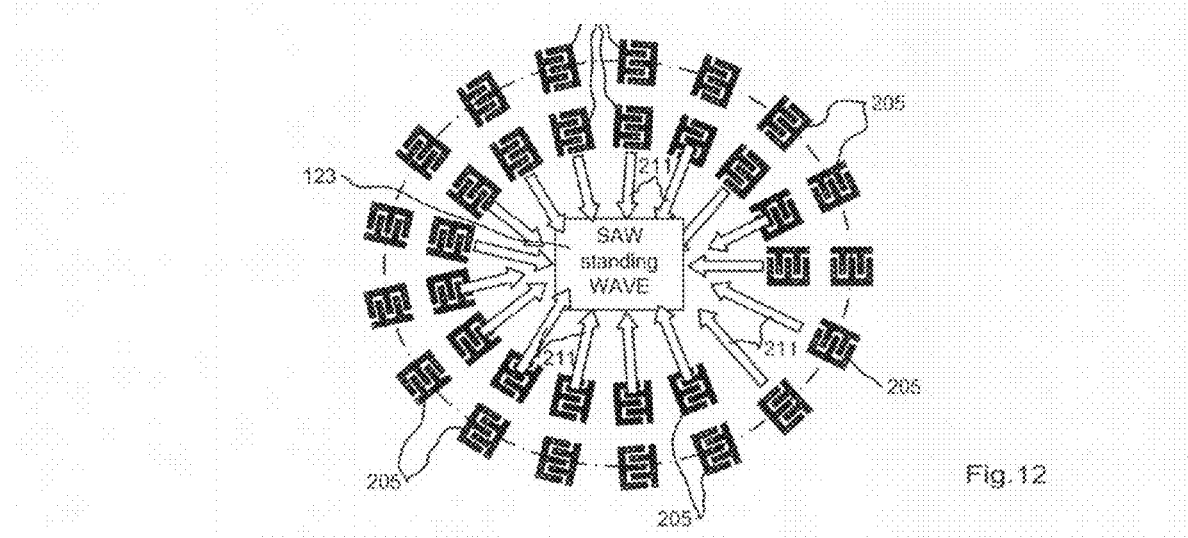
FIG. 12 is an illustration of IDT actuators placed in a circular configuration in accordance with another embodiment of the present invention.

Reference is now made to FIG. 12, which is an illustration of another embodiment of the present invention, wherein SAW focused standing waves 123 are created with serial IDT 205 actuators placed in a circular configuration. This type of configuration may be useful for IDT 205 actuators, since IDT 205 actuators tend to create weak SAW; thus, it may be advantageous to focus the energy concentration. By placing IDT 205 actuators in a circular configuration, running waves propagating in a direction shown by arrows 211 (to the center of the circular configuration) will interfere with each other in the center, thus creating an area of standing waves 123 with much higher acoustic power.

Figure 13:
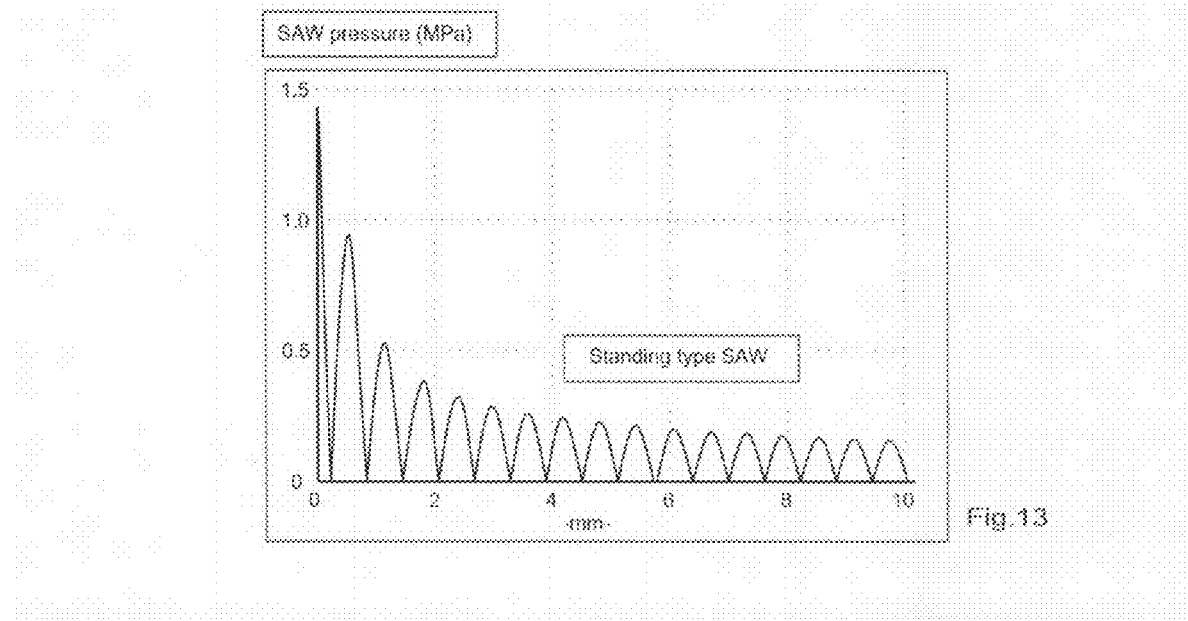
FIG. 13 is a graphical illustration of pressure from a focused standing wave versus distance from the center for high frequency acoustic waves obtained when actuators are placed circularly, as depicted in FIG. 12.

Reference is now made to FIG. 13, which is a graphical illustration of pressure from a focused standing wave versus distance from the center for high frequency acoustic waves obtained when actuators are placed circularly, as depicted in FIG. 12. The pressure greatly increases in the central zone due to the focusing effect.

A focused effect such as the one described above with respect to FIGS. 12 and 13 may also be obtained by using a ring-shaped piezo-element for activating portion 282 of actuator 200. Running waves are directed inwardly, towards a center of the ring-shaped piezo-element. Interaction of these running waves with one another causes formation of standing waves at the center. The minimal thickness of a ring-shaped piezo-element for this purpose may be in the order of 0.05 mm to 0.1 mm. The inner radius of the ring-shaped piezo-element may be in the order of 1-100 mm. Other dimensions are possible as well. In some embodiments, the ring-shaped piezo-element has an outer layer, which may be, for example, an absorbing material such as rubber, silicone, polymer or metal or any other suitable absorbing material. The absorbing material may be adapted to absorb the acoustic vibrations which are directed outwardly from the ring, if it is desired. As in all of the actuators of the present invention, a power supply system may be adapted to supply electric input to the ring-shaped piezo-element. The frequency of the electric input may be selectively controlled. Electric input from the power supply may be delivered to the conductive material of the ring-shaped piezo-element, which may then cause substantial vibrations of the ring-shaped piezo-element. For example, the electric input delivered to the ring-shaped piezo-element may cause thickness, longitudinal, or torsion or any other acoustic wave form. The selected frequency may be dependent upon various system parameters, including, but not limited to the thickness of the piezoceramic material used for ring-shaped piezo-element. For example, the frequency applied to a ring-shaped piezo-element having a thickness of 0.05 mm may be approximately 20 MHz and the frequency applied to a ring-shaped piezo-element 220 having a thickness of 50 mm may be approximately 0.1 MHz, since the frequency is inversely related to the thickness of the material. That is, a thicker material will be excited with a lower frequency than a thin material. Other frequencies and thicknesses may be selected. In some embodiments, the ring-shaped piezo-element is constructed of several arc sections, which may be excited simultaneously or sequentially, or in any other combination, resulting in lower energy assumptions with higher focused results. In some embodiments, serially positioned ring-shaped piezo-elements may create multiple areas of focused SAW effects.

Reference is now made to FIG. 14A, which is an illustration of an embodiment of the present invention, showing creation of SAW focused standing waves using a ring-shaped piezo-element 220, as shown in FIG. 14B. Ring-shaped piezo-element 220 is placed on device 100. When stimulated, SAW form outwardly and inwardly with respect to ring-shaped piezo-element 220, as depicted by arrows 211. This causes a focusing of running waves at a center area resulting in standing SAW in a focused area 225 as depicted in FIGS. 14A and 14B, and may create extremely high pressure or temperature at focused area 225.

Reference is now made to FIG. 15, which is a schematic illustration of SAW generation on a device 100. The device 100 shown herein is a urinary catheter 101, but it should be readily apparent that the following description applies to many devices. Actuator 200 is comprised of a thin piezo-electric (PZT) plate element 210, which is attached to catheter 101. Processor 300 is a driver which provides periodic electrical pulses to PZT plate element 210, which results in mechanical vibrations in normal modes. PZT plate element 210 is attached to an external surface 110 of catheter 101, and is connected via a cable 320 to processor 300. An electrical signal from processor 300 excites bi-directional vibrations in PZT plate element 210, as shown by arrows 211 and 212. The sum of the bi-directional vibrations is a bending vibration mode, depicted by sinusoidal lines 219 having maximum points on each side, as depicted by points 213 and 214. Maximum points 213 and 214 generate mechanical vibrations on the device surface 110.

A distance 215 between maximum points 213 is chosen to be equal to one-half the length of the SAW. Similarly, a distance 216 between maximum points 214 will also be equal to one-half the length of the SAW. In this way, a running wave is excited on surface 110 in directions shown by arrows 910 and 920. These SAW are low-energy and fade with depth. Their physical motion causes a time-dependent elliptical displacement of device material particles, as shown by broken arrows 911 and 921. One longitudinal vector spreads parallel to the wave propagation x axis along the surface of the catheter, triggering horizontal surface particle displacement ($U_R$) 217. The length of surface wave $U_R$ is equal to two distances 215 or 216 of piezo ceramic vibration. Another transversal compression wave component ($W_R$) 218 develops on the y axis normal to the device surface causing displacement in the direction of surrounding tissues or fluid. The amplitude of this wave $W_R$ is shown as distance 218.

SAW excited on the device have a first direction 910 and a second direction 920 of the propagating wave and may be assumed to be Rayleigh type waves. Rayleigh type acoustic waves cause the device surface particle oscillations in directions that are parallel to the wave propagation x axis ($U_R$) along the surface and normal to the surface—y axis ($W_R$). Calculation of velocity and amplitudes of these particle oscillations is as follows:

$$U_R = Ak_R \left(1 - \frac{2q_R S_R}{k_R^2 + S_R^2}\right) \sin(k_R x - \omega t)$$

$$W_R = Aq_R \left(1 - \frac{2k_R^2}{k_R^2 + S_R^2}\right) \cos(k_R x - \omega t)$$

where $q_R^2$, $S_R^2$ and A are constants calculated as follows: $q_R^2 = k_R^2 - k_t^2$ and $S_R^2 = k_R^2 - k_e^2$, $k_R$ denotes Rayleigh wave numbers on the surface, $k_e$, $k_t$ are the numbers of longitudinal and transversal waves respectively $k_e = 2\pi f/c_e$ and $k_t = 2\pi f/c_t$ ($c_t$ being the longitudinal and $c_e$ the transversal acoustic velocities), $k_R = k_t/\eta_R$ and $\eta_R = (0.87 + 1.12\sigma)/(1+\sigma)$, where $\sigma$ is the Poisson ratio.

It has been found in the present invention that the parameters that define the SAW to prevent microbial biofilm development are as follows: peak maximum particle displacement motion ($W_R$) of surface components excited on the x axis with elastic waves at a frequency of 100 kHz is 2 nm. ($U_R$) calculated on the y axis from formulas provided above, equals 3.73 nm. The velocity of surface point movement $V_x = 0.0023$ m/sec, the corresponding acceleration $a_x = 1472.2$ m/sec$^2$, the y axis velocity $V_y = 0.0013$ n/sec and the acceleration $a_y = 789.6$ m/sec$^2$. The velocity of Rayleigh acoustic waves $C_r = 28.324$ m/sec.

When the surface acoustic wave-generated particle relative elliptical oscillation amplitudes are smaller than the potential repulsive zone, an overall net repulsion occurs. This may cause inhibition of particle attachment to the surfaces, inhibition of adhesion, growth and aggregation of cells into micro-colonies on the surfaces, and inhibition of maturation and dissemination of progeny cells for new colony formation.

The mechanical amplitudes of SAW, which are of running wave types, are in a range of approximately 0.1-5 nanometers with frequencies ranging from about 100 KHz-1 MHz. The velocities of these running wave ranges from 14-30 m/s, and the magnitudes are close to acoustic wave velocity in the skin, thereby preventing irritation of the tissue.

Particles and bacteria on the device surface are forced in an opposite direction respective to the vibration transmission direction, thereby forcing them out of the zone. Consequently, external surfaces 110 of device 100 are covered with a virtual nanovibrating coat.

Reference is now made to FIG. 16, which is a schematic illustration of device 100 positioned next to a body tissue 400, and depicting SAW in motion and its effect at different depths within tissue 400. SAW are created in a first direction 910, and the physical motion of SAW is associated mechanically with a time-dependent elliptical displacement of surface material particles as shown by ellipses 506.

An elastic organic material 410 is positioned between external surface 110 of device 100 and tissue 400. Elastic organic material 410 may be, for example, mucosa, a drug, or a topical cream, for example. SAW are propagated at the interface between external surface 110 of device 100 and elastic organic material 410.

SAW cause micro-motion of the particles and liquids on external surface 110 of device 100 in a second direction 920, that is along the same axis but in an opposite direction to first direction 910 (i.e. direction of wave propagation). This phenomenon, created by SAW, is characteristic to all materials and is effective until a depth of distance 913. The greatest micro motion in second direction 920 is at the area of nearest proximity to external surface 110, and it gradually decreases in tissue 400 along the length of distance 913.

Particles or bacteria attempting to infiltrate the surface in a direction shown by arrow 700 are prevented from entering due to the micro motion in second direction 920. Thus, bacteria are directed out of the wound zone. The velocity of particle motion in second direction 920 is about 1 mm/h, which is greater than the velocity of mobile bacteria, thus preventing bacteria from entering.

The shear vertical component 914, known as transverse energy, of the SAW causes periodic compression and rarefaction of the materials and fluids, resulting in transmission of acoustic energy from the surface to surrounding tissues. The relation for this is a function of the surface wave length and shear wave length.

The shear vertical component of the SAW results in micro massage. The effect may be understood as a mechanical effect of acoustic energy traveling through the medium and causing the molecules to vibrate. The above effects will likely have an influence on the general state of the patient tissues and may enhance the healing processes in post surgery patients by enhancing tissue fluid interchange.

The transverse energy may be transferred to the tissues of the human body from external surface. The vibration amplitudes decrease exponentially with distance from the interface. The energy of a SAW (Rayleigh wave) is localized along a distance 913 within tissue 400, wherein the distance ranges from $\lambda_R$ up to 2 $\lambda_R$, where $\lambda_R$—is the length of Rayleigh wave. In the embodiment shown in FIG. 16, the depth of SAW propagation in the direction of tissue 400 or organic material 410 reaches up to 2 wavelengths (less then 1 mm).

The transverse vibration energy affects the fluids in contact with device 100, and the friction of the fluids is reduced; moreover, the vibration may expel the fluid and cause drying at the interface, which slows or prevents the entry of bacteria, and enhances the healing process.

In summary, actuator 200 creates an acoustic energy transmission line towards the liquid and body tissues 400 in acoustic contact with device 100. The energy transmission may have two components: a) at a depth equal to two surface wave lengths towards the body tissue 400, the tissue particles are mechanically-elliptically oscillating, with velocities of tenths meter/second; b) at a depth exceeding two surface wave lengths towards body tissue 400, the particles are lineally-mechanically oscillating, with nanometer amplitudes. Positive effects on tissues may be seen.

Additional embodiments of actuators which may be used in the present application are disclosed in U.S. Patent Publication No. 2005/0268921; U.S. Patent Publication No. 2005/0095351; and U.S. Patent Publication No. 2005/0038376, all of which are incorporated by reference herein in their entireties.

2. SAW Applications for Indwelling Medical Devices
Catheters

Catheters are widely used in medical applications, e.g., for intravenous, arterial, peritoneal, pleural, intrathecal, subdural, urological, synovial, gynecological, percutaneous, gastrointestinal, abscess drains, and subcutaneous applications. Intravenous infusions are used for introducing fluids, nutrition, blood or its products, and medications to patients. These catheters are placed for short-term, intermediate, and long-term usage. Types of catheters include standard IV, peripherally inserted central catheters (PICC)/midline, central venous catheters (CVC), angiographic catheters, guide catheters, feeding tubes, endoscopy catheters, Foley catheters, drainage catheters, and needles. Catheter complications include phlebitis, localized infection and thrombosis.

Indwelling devices, when inserted into the body, are coated with a conditioning film. Vascular catheters are coated with fibrin and fibronectin, while urinary catheters are encrusted with proteins, electrolytes and other organic molecules which are part of the urine content. The conditioning of the indwelling device makes the catheter surface more hospitable to biofilm formation although bare catheters are also susceptible to the development of biofilm. Although indwelling catheters are meant to operate in a sterile environment, biofilm still forms on catheters. In catheter-associated urinary tract infection (CAUTI) 66% of the microorganisms gain access to the bladder extraluminally (direct contamination during catheter insertion or by capillary action ascending from the perineal area) and 34% intraluminally (ascending microorganisms from a contaminated urine bag).

Catheters are optionally placed anywhere in the body (i.e., the class of catheters comprises more than just IVs) and are typically plastic, which is strong enough to place in, e.g., a vein, but flexible enough to bend within the patient's body. It is typically desired to reduce catheter care (e.g., replacement time) and to decrease catheter contamination, e.g., from skin "crawling down," biofouling, etc. It is also desirable to avoid phlebosis or any problem disturbing flow which can arise through use of a "flush" to blow clots, etc. downstream.

In the present invention, generation of surface acoustic elastic Rayleigh waves with horizontal and vertical propagation vectors, the pressure amplitude of which is highly regulated, can prevent microbial biofilm formation irrespective of the type of microorganism. The prevention is mechanical and interferes effectively with attachment of the planktonic bacteria to solid substrates, the first step in bacterial biofilm formation. The mechanical characteristics of the described invention make it possible to overcome the obstacle of a conditioning film. In some embodiments, the acoustic energy must be applied continuously throughout the duration of patient catheterization since disruption of the energy supply may be associated with bacteria resuming adhesion to surfaces and initiation of biofilm development. Once attachment has occurred, resuming the SAW treatment is unlikely to prevent the differentiation of attached bacteria into a biofilm, although it is likely to prevent de novo attachment of additional planktonic bacteria and in this sense to limit the expansion of the biofilm formation process.

In-vitro tests in which SAW reduced the biofilm burden on the catheter segments which were immersed in different microbial suspensions have shown that SAW can affect different microbes (gram positive, gram negative and a fungi), indicating that SAW mechanism of action is not specific. In these experiments SAW was activated in an initially contaminated environment ($10^4$ CFU/ml), and despite these conditions managed to reduce biofilm. These findings indicate that the effect of SAW is purely mechanical, wherein SAW interfere with bacterial adhesion.

Therefore, in various embodiments herein, actuators of SAW may be used in, on or within catheters and related medical devices. The bacteriostatic characteristics of catheters with SAW actuators applied herein can optionally decrease infection, while the hydrophobic characteristics can optionally increase fluid flow properties. The anti-thrombotic characteristics of such devices can optionally decrease thrombosis—a condition which leads to catheter plugging and emboli.

Thus, it is a purpose of the present invention to provide catheter systems with decreased infection, increased flow and decreased clot formation resulting from use of SAW actuators. Such features can optionally lead to reduction in catheter complications and an increase in the amount of time a catheter could remain in place before having to be replaced.

The antifouling aspects of the current invention are also optionally useful in catheters used for wound drainage. Such catheters typically present problems with bacterial contamination. Use of the embodiments of the invention can, thus, reduce drug use (e.g., antibiotics), reduce pain, reduce need for further operations, and reduce infection rates. As explained herein the catheters of the invention are also optionally coated with compounds, e.g., silver compounds, titanium oxides, antibiotics, and the like, which can further help in reducing infection.

Reference is now made to FIG. 17, which is an illustration of a central venous catheter system 330 inserted into a body 405 of a patient. Central venous catheter system 330 is threaded through a vein in the neck (the external or internal jugular vein) or a vein 407 in the upper chest under the collar bone (the subclavian vein) into a large central vein in the chest (the superior vena cava). The two general types of catheter systems which are permanently placed under the skin are internal catheters, which are completely enclosed, and external catheters, which exit through the skin. By generating SAW, the vibration of the surface material of catheter system 330 results in a decrease in the coefficient of friction of the material of catheter system 330, which improves biocompatibility by reducing frictional irritation and cell adhesion at the biomaterial—tissue interface. The process of precipitation and formation of crystals (accelerated kinetically by the presence of rough surfaces, catheter holes and edges) is also reduced.

As shown in FIG. 17, in one embodiment, two thin piezo-elements 204 are attached at separate locations on central venous catheter system 330. A first thin piezo element 204A is incorporated into a pad 331, and a second thin piezo element 204B is attached as a clip-on to an external portion of catheter system 330. The two piezo-elements 204 are in electrical communication with processor 300, which is located outside of the body 405. First piezo-element 204A is configured to provide an infection-free environment at the insertion site—adjacent to an internal location of catheter system 330, and to help heal the catheter insertion wound. Pad 331 may be, for example, a disinfecting pad placed at the insertion site prior to introducing the catheter. In addition, pad 331 may be left in place during healing, preventing bacterial infection during that phase. Second piezo-element 204B creates SAW on internal and external surfaces of central venous catheter system 330 and possibly on the hub or connector of the system to inhibit biofilm formation in critical device construction areas.

Reference is now made to FIG. 18, which is an illustration of pad 331 enlarged. In addition to disinfecting action prior to catheter insertion, pad 331 may also be used as a hydrophilic wound dressing that is used to absorb exudates and cover a wound caused by the use of vascular and other medical devices (IV catheters, CVL, arterial catheters, dialysis catheters drains, externally placed orthopedic pins). It is also useful in reducing local infections, catheter related blood stream infections, and skin colonization of microorganisms. As shown in FIG. 18, pad 331 with actuator 200 positioned thereon is placed in contact with the skin 415 of an individual. Actuator 200 causes SAW to propagate in a pre-determined direction on skin 415, as shown by arrow 211 or on structures located beneath the skin, such as veins 407 or arteries. The energy levels are controlled via processor 300, and may be altered by medical professionals. The same piezo-element which is located on pad 331 may also excite SAW on the surface and simultaneously may cause longitudinal and transverse vibrations, which are used as traditional ultrasound treatment.

Endoscopes

One of the more difficult aspects of endoscopy, e.g., colonoscopy, involves the frictional resistance of the device passing through the tubular organ, e.g., bowel, urethra, esophagus, trachea, blood vessel, etc. Besides being difficult to transport the scope or catheter, the friction causes significant discomfort to the patient. Slippery catheters, coated with, for example, polyvinylpyrolidone have been designed to provide easier passage but these devices have not enjoyed wide market acceptance. A lubricious scope or catheter comprising SAW excited on the device of the invention, would be expected to provide significantly increased patient comfort and more facile transport for the physician.

In some embodiments, multiple actuators may be used. For example, a first actuator may be placed on an external surface of the endoscope to clean the sensing surface of the endoscope and to decrease friction, a second actuator may be placed on an internal surface of the endoscope to decrease friction on both internal and external surfaces of the endoscope, and a third actuator may be placed on a light guide loop to decrease friction in the light guide loop.

Syringes and Needles

Cutting needles or scalpels are optimized when serrated and sharpened. However, protein attachment to the surface of such needles may create effective dullness, even on the sharpest of needles. Thus, application of SAW to needles or scalpels can restore sharpness to such devices which may be lost due to protein attachment and may also have the effects of decreased friction, pain, and prevention of bacteria adhesion. Actuators and processors according to embodiments of the present invention may be attached to medical syringes or needles. SAW may be propagated on a metal end of a syringe and further propagated through the needle's external and internal surfaces. In one embodiment, the kinetic energy of liquid located within syringe may be used as a power source for activation of an actuator placed thereon. Additionally, the needles themselves may be manufactured using materials having piezoelectric properties. In yet additional embodiments, SAW actuators may be used for sensing and monitoring of dynamic properties of blood or depth of penetration of a needle, for example, since dynamic blood properties have an influence on needle loading. Changes in needle loading forces may be sent as a feedback signal to processor 300 and monitored. In some embodiments, actuators may have a dual role of exciting SAW and sensing parameters. Processor 300 may include a battery power supply or a separate power supply. In some embodiments, an actuator 200 and/or sensor is attached to the syringe or needle. In other embodiments, the syringe or needle is made of piezoelectric material and acts as actuator 200 and/or a sensor. SAW actuators are configured to excite SAW on the surfaces of the device 100, and as SAW transverse components on the surfaces of body organs, and in liquids in the body.

Figure 19:
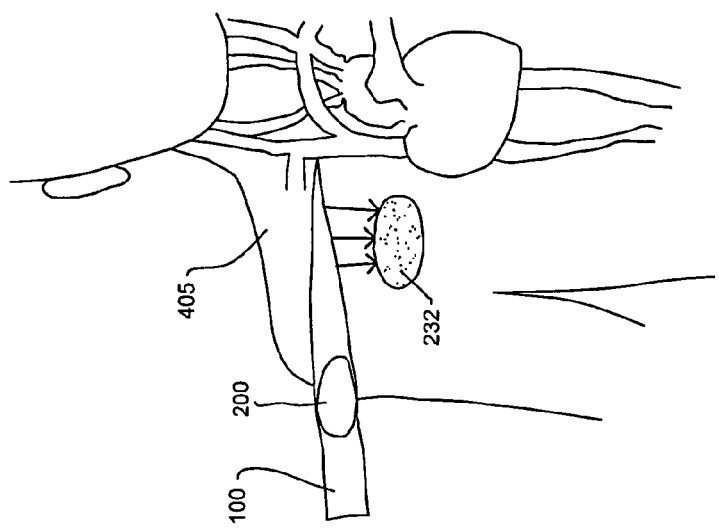
FIG. 19 is an illustration of a syringe with an actuator and a separate sensing device.

Reference is now made to FIG. 19, which is an illustration of a syringe with an actuator 200 positioned thereon and a sensing device 232 separately configured. For example, sensing device 232 may be attached to the body 405, and may include a receiver and a transmitter. Sensing device 232 is configured to receive compression waves from the surfaces that have been excited with SAW. Sensing device 232 may be an acoustic sensor, such as those known in the art and used to measure biofilm thickness based on differences in acoustic wave velocity. Sensing device 232 senses mechanical vibration input transmitted from the surface of device 100, and works using a direct piezo-electric effect, wherein it produces an electrical signal which is proportional to the mechanical vibration input. In addition, existing data on the differences in acoustic signals with and without biofilm can be used to compare obtained acoustic signals and determine whether biofilm exists or not. In some embodiments, sensing device 232 is configured as a patch which can be directly adhered to the body at the area of interest.

Figure 20:
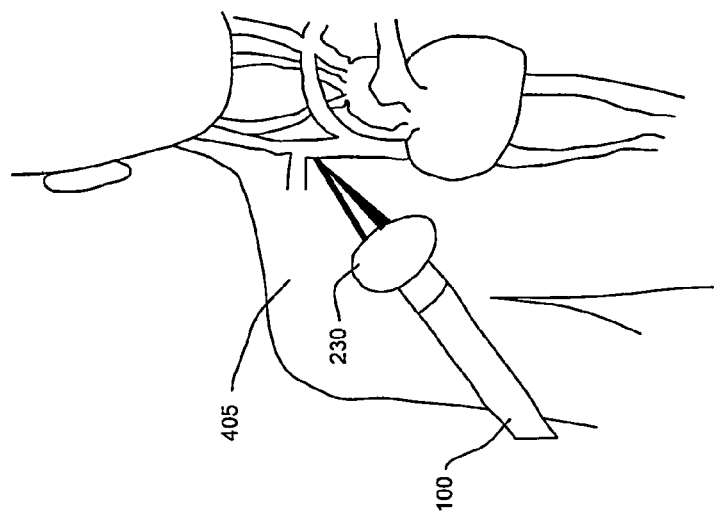
FIG. 20 is an illustration of a combination actuator-sensor with a power supply incorporated therein.

Reference is now made to FIG. 20, which is an illustration of a combination actuator-sensor 230, wherein a power supply is also incorporated within actuator-sensor 230. Actuator-sensor 230 is attached to device 100, and preferably at or near a location of device 100 which is configured to enter the body. In some embodiments, as shown in FIG. 20, a battery-operated actuator-sensor 230 is implanted within the body at a location wherein device 100 is configured to enter the body.

In some embodiments, actuator 200 (or actuator-sensor 230) receives energy for the SAW process from body movements instead of or in addition to a battery. For example, movements of the hands or legs, breathing, pumping of the heart, or blood flow all provide kinetic energy which can be harnessed for use in powering actuator 200. This can be done for an actuator which is implanted or which is attached to device 100. The principle is analogical to one used in hand watches, wherein kinetic energy of hand movements (or foot stepping, or heart beating) is accumulated in spring potential energy. This mechanical energy may excite a direct piezo effect in the piezoelectric material of actuator 200, resulting in electrical energy. The electrical signal may be transmitted to the electrodes of actuator 200, exciting the piezoelectric material of activating portion of actuator 200 to vibrate (reverse piezo effect). Alternatively, the electrical energy obtained due to the direct piezo effect may be accumulated and stored in a battery, and further used for the excitement of actuator 200. Biomechanical properties of body movements provide a potential to excite mechanical energy in the range 0.1 Hz-2 KHz.

External Fixators

External fixators are pins and wires inserted through the skin into bone for the purpose of healing bone fractures. These pins and wires are then connected externally with rods and clamps in order to provide rigidity and stability so the fractured bone can heal. The advantage of these devices over internally placed plates, screws, pins and wires is in the decreased amount of tissue and vascular disruption caused when compared to surgical placement of internal implants. This lesser surgical invasion allows the fracture to heal much faster and with less muscle and subcutaneous scarring, implant-related osteosarcomas, osteoarthritic changes, or painful cold-sensation complications and obviates the need for surgical implant removal at a later date. Complications arising from the use of external fixators are bacterial infection from the skin, and excessive movement of the pins if the connecting apparatus is insufficiently stable. The use of devices with SAW can be advantageous in correcting these potential complications. In some embodiments, the entire surface is coated with SAW, while in other embodiments, only portions such as the screw threads, pins, or bonding areas are coated with SAW.

3. SAW Applications for Implants

For implants, SAW may only be applied for short periods of time for enhancement of tissue ingrowth or prevention of bacteria adhesion at the outset. As such, a relatively small battery may be used to provide power to an actuator used for implants. Implants with SAW may provide therapeutic action or may result in decreased friction which may be beneficial during introduction and/or removal of the implant.

Figure 21:
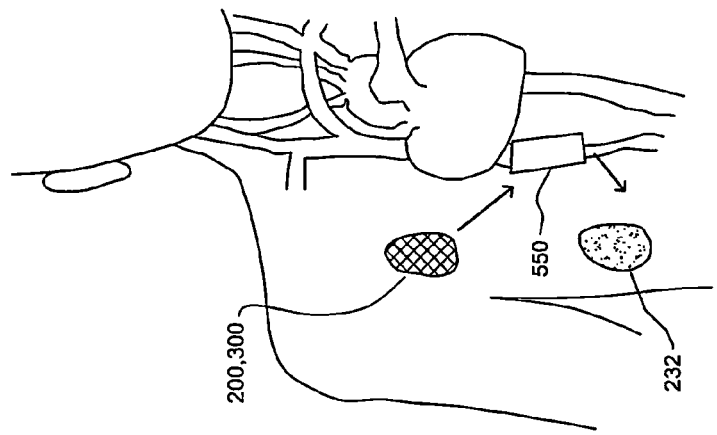
FIG. 21 is an illustration of an implant positioned within the body.
Figure 22:
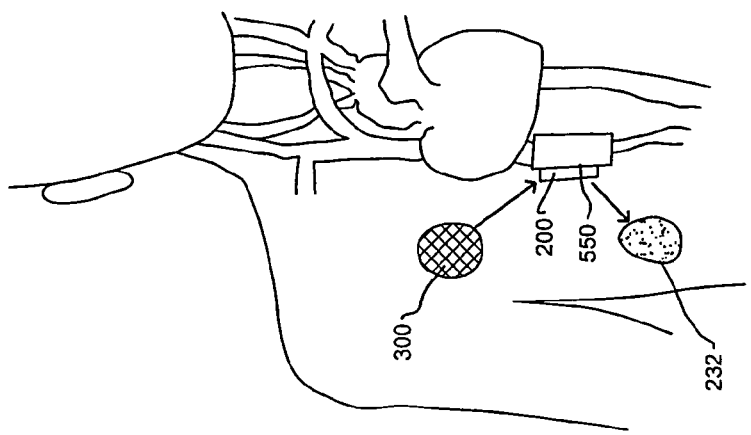
FIG. 22 is an illustration of the implant of FIG. 21, wherein an actuator is incorporated within or onto the implant, and a processor and sensing device are placed external to the body.

Reference is now made to FIG. 21-24, which are illustrations of various embodiments of implants treated with SAW. As shown in FIG. 21, implant 550, which may be any type of implant, is positioned within the body. Actuator 200 and processor 300 are attached to the body (externally), and are configured to excite SAW through the body and onto the surface of implant 550. In some embodiments, sensing device 232 is also placed on the body at a different location. Both actuator 200 (with processor 300 incorporated therein) and sensing device 232 may be configured, for example, as patches. In other embodiments, as shown in FIG. 22, actuator 200 is incorporated within or onto implant 550, and only processor 300 and optionally sensing device 232 are placed external to the body.

Figure 23:
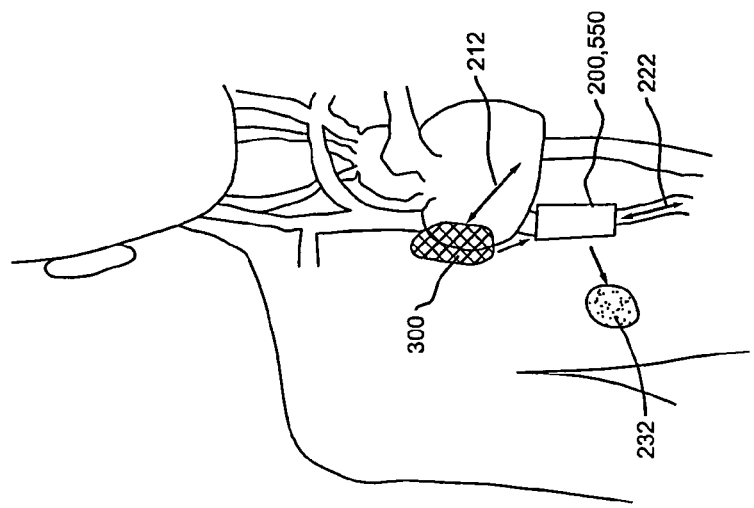
FIG. 23 is a depiction of energy obtained through body natural acoustic energy transmission lines.

In some embodiments, as depicted in FIG. 23, energy is obtained through body natural acoustic energy transmission lines. This may be achieved while applying vibrational energy adjacent to a target organ or adjacent to a natural body conduit transmitting the energy to the target. Several such natural conduits include: epidermis, subcutis, fascia, muscle and sarcolemma, trachea, the valves and fibrous heart skeleton, etc. In the embodiment depicted in FIG. 23, implant 550 is comprised of piezoelectric material, and thus acts as actuator 200. The acoustic energy of the body tissues or organs such as pumping of the heart, depicted by arrow 212 or blood flow, depicted by arrow 222, excites implant 550, which in turn causes creation of SAW, as described above.

Mechanical Heart Valves

There are two types of heart valve prostheses used for replacement of aortic and mitral valves. Mechanical valves commonly are metallic cages with a disc that opens at systole to allow blood to flow and closes at diastole to prevent backflow. These valves last indefinitely but require the daily administration of an anticoagulant drug to prevent thrombotic complications. The dose must be carefully regulated to prevent thrombus formation on one hand and internal hemorrhage on the other. The second type of valve is a tissue valve, sometimes isolated en bloc from porcine hearts and sometimes constructed from bovine pericardial tissue. These leaflet valves are more like natural valves and usually do not require anticoagulant drug administration. However, they are susceptible to degradation and have more finite life expectancies than do the mechanical valves. Fortunately, they fail slowly and provide ample time for surgical replacement. Moreover, flow eddies are created downstream of the hinge seat for some bi-leaflet valve designs, which may be related to thrombogenicity. Thus, in embodiments of the present invention, SAW are used to improve the hemodynamic performance of left ventricular assist devices (LVADs), including improved blood throughput, reduction for a need for anticoagulation therapy, reduced incidence of thrombosis and reduced hemolysis.

Figure 24:
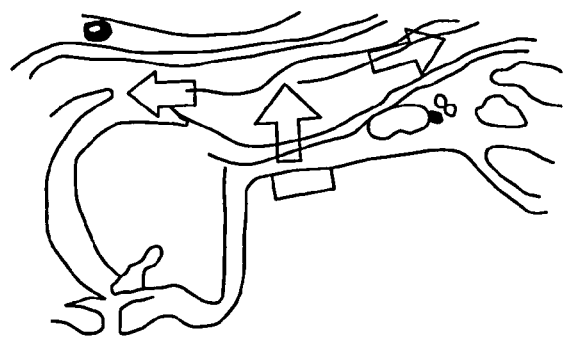
FIG. 24 is an illustration of an actuator placed externally in the area of the neck.
Figure 25B:
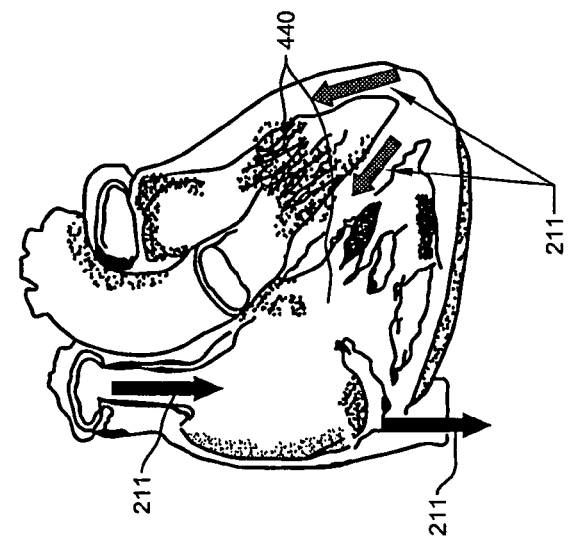
FIG. 25B is an illustration of the vibrations of FIG. 25A propagating into the heart valves.
Figure 25A:
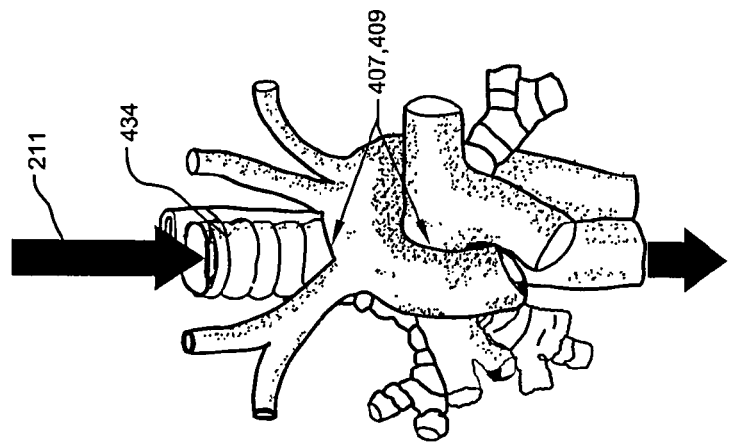
FIG. 25A is an illustration of vibrations being delivered down the trachea.

Reference is now made to FIGS. 24-25, which are illustrations of a mechanical heart valve 560 treated with SAW. As shown in FIG. 24, actuator 200 may be placed externally in the area of the neck—directly over the Adam's Apple. Actuator 200 is firmly attached to the neck by taping it with medical tape, for example. Natural acoustic lines exist in the body which can conduct acoustic energy, for example, the trachea 434. Upon activation of actuator 200, vibrations are delivered down the trachea 434, as shown in FIG. 25A via arrow 211. These SAW are distributed along natural body conduits such as veins 407 and arteries 409, to eventually reach an arch of the aorta and pulmonary artery, propagating therethrough and into the heart valves 440, as shown in FIG. 25B and depicted by arrows 211. All of the heart valves are connected to a fibro-elastic tissue that separates the ventricles from the atria. These structures are effective transmitters of vibrations and act as natural conduits.

Small Caliber Vascular Grafts

The ultra non-wettability of SAW may have a positive effect on vascular grafts in at least two ways. First, SAW may help to eliminate deposition of plasma protein on the luminal surface, thus preserving the original graft diameter. Secondly, SAW may greatly improve laminar blood flow which can aid in reduction of luminal thrombus formation. Thus, known causes of graft failure such as graft thrombosis and anastomotic intimal hyperplasia may be avoided.

Abdominal Aortic Aneurysm (AAA) Medical Procedures

An aortic aneurysm generally is an abnormal widening, stretching or ballooning of the thoracic or abdominal portion of the aorta, which is the major artery from the heart which delivers blood to the major organs of the body. The thoracic and abdominal portions of the aorta represent the upper, arched portion and lower, abdominal portion of the aorta, respectively. The exact cause of aneurysm is unknown, but risks include atherosclerosis and hypertension. A common complication is ruptured aortic aneurysm, a medical emergency in which the aneurysm breaks open, resulting in profuse bleeding. Aortic dissection occurs when the lining of the artery tears and blood leaks into the wall of the artery. An aneurysm that dissects is at even greater risk of rupture. Generally, when an abdominal or thoracic aortic aneurysm reaches a size of about 5 cm, surgical intervention is necessary. To repair an abdominal or thoracic aortic aneurysm by intraoperative procedure, the thoracic cavity can be accessed by a midline or retroperitoneal incision in the case of an open procedure, or by percutaneous access in a minimally invasive endograft procedure, and an autogenous or prosthetic graft is used to isolate the aneurysm from blood flow and pressurization, thus precluding aneurysm expansion and minimizing the risk of rupture. Typically, the first choice for replacement is typically the autogenous saphenous vein (ASV), but when it is unavailable for transplant, artificial prosthetic grafts may be used. Generally they are used for large diameter vessel applications such as aortic aneurysm repair, however recent research efforts have been directed towards finding suitable methods for medium and small diameter vessel repair as well.

Inaccurate deployment of aortic prostheses can lead to inadequate sealing of the aneurysm which can cause further aneurysm expansion due to blood flow around the graft, and/or inadvertent blockage of collateral vessels supplied by the aorta, for example, such as the renal arteries. Aortic prostheses can also slip out of position. A need exists to improve the outcome of aortic aneurysm repair by improving the materials of the grafts to make them more adherent thereby minimizing or eliminating failures of conventional devices caused by such complications as leakage and/or mal-positioning or slippage of the prosthetic devices.

Using the methods and compositions disclosed herein, both open and minimally invasive endovascular repair procedures can be performed to ensure that an aortic prosthesis, when placed properly at the site of an aneurysm, will adhere firmly to the tissue surface and maintain its patency for longer periods of time than conventional devices. The outer (and/or inner) diameter of the graft prosthesis is coated with SAW, thus providing the graft with a dry adhesive surface. The disclosed methods described above and herein can provide enhanced accuracy, for example, with respect to location and orientation, in the placement of the prostheses within a region of a patient's aorta having an aneurysm or other diseased or damaged condition therein.

Although the techniques of the present invention can be used to facilitate both open and minimally invasive abdominal or thoracic aortic aneurysm procedures (or any other aneurysm procedure in the aorta or other areas of the body as well), the following illustration describes only an endovascular minimally invasive repair procedure which is less traumatic to the patient than an open-chest procedure. One of ordinary skill in the art, however, will appreciate that the techniques disclosed can be readily applied to open chest procedures as well in which access to the thoracic cavity is achieved through a midline partial or median sternotomy, a mini-thoracotomy incision, or a retroperitoneal incision, for example.

Figure 26A:
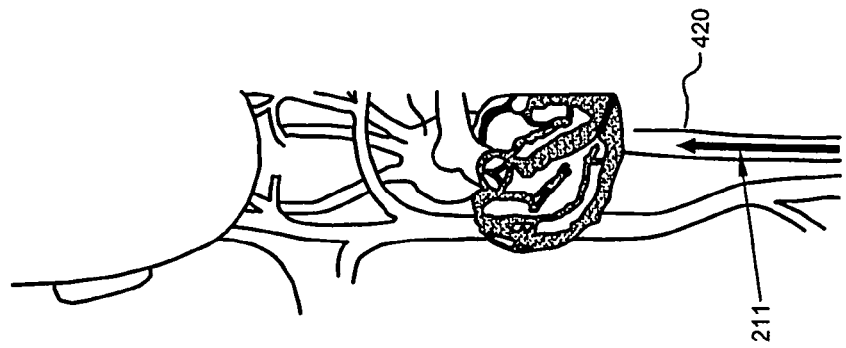
FIGS. 26A and 26B are schematic illustrations of a system for placing a prosthetic graft during a closed-chest abdominal or thoracic aortic aneurysm repair procedure using the methods of the present invention.
Figure 26B:
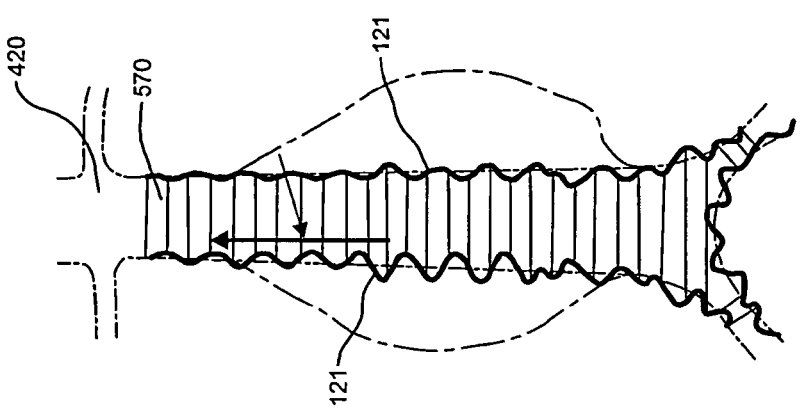

Referring now to FIGS. 26A and 26B, a system is schematically illustrated for placing a prosthetic graft 570 during a closed-chest abdominal or thoracic aortic aneurysm repair procedure using the methods of the present invention. In one embodiment, a patient is anesthesized and generally prepared for surgery in a conventional manner. The procedure then involves positioning a delivery device and graft 570 within the abdominal aorta 420 at the site of the aneurysm. The embodiments of the present invention include SAW of Rayleigh and/or "pseudo" Rayleigh, and/or Lamb types on graft 570. Actuator 200 is integrated with or coupled to a proximal end of the delivery device. By activating actuator 200, SAW 121 are excited on internal and external surfaces of graft 570. SAW on the external surface reduce friction and aid in delivery. The reduction of friction occurs due to decreased contact time between the device surface and tissue points, thus resulting in better liquid delivery. Additionally, therapeutic action may be accomplished by activation of SAW on external surfaces once graft 570 is in place. The therapeutic action occurs due to acoustic micro streaming and better moisture exchange between cells. In some embodiments, a sensor is also included.

SAW on the external surface reduce friction and aid in delivery. The reduction of friction occur due to decreased contact time between device surface and tissue points, thus resulting in better liquid delivery. Additionally, therapeutic action may be accomplished by activation of SAW on external surfaces once graft 570 is in place. The therapeutic action occur due acoustic micro streaming and better moisture exchange between cells. In some embodiments, a sensor is also included.

Endovascular devices which can be used for aortic aneurysm repair include, for example, balloon-expandable or self-expandable devices. The following devices are examples of systems that can be used together with actuator 200 of the present invention: Ancure® Endograft® System (Guidant Corporation); Ancure® Aortoiliac System (Guidant Corporation); AneuRx® Stent Graft System (Medtronic AVE); EXCLUDER™ Bifurcated Endoprosthesis (W. L. Gore and Associates, Inc.); Zenith™ AAA Endovascular Graft and H&L-B One-Shot™ Introduction System (Cook, Inc.). These systems generally include both a graft and a corresponding delivery catheter. It should be readily apparent that any suitable graft and delivery catheter may be used, and that the present invention is not limited to the examples listed above.

In some embodiments, graft 570 is comprised of piezoelectric material and may further include a biocompatible material layered on the piezoelectric material. Activation of actuator 200 accomplished by harnessing the kinetic energy of blood flow and converting the kinetic energy into electrical energy by direct or reverse piezoelectric effect as described above. Graft 570 may be comprised of, for example, treated natural tissue, laboratory-engineered tissue, and synthetic polymer fabrics. Synthetic polymers include, for example, Dacron® and Teflon® (i.e., expanded polytetrafluoroethylene (ePTFE)), poly(alpha-hydroxy ester)s, polyanhydrides, polyorthoesters, polyphosphazens, tyrosine-derived polycarbonates and polyarylates, lactide based polydepsipeptide polymer, poly(L-lactide acid-co-L-aspartic acid), and lactide based poly(ethylene glycol). Metals such as stainless steel, titanium, or Nitinol metal mesh or other biocompatible metals may also be used as the synthetic graft material, as well as other alloys. In addition, the graft may be coated with a thin piezo material layer comprising PZT 5 or PZT 6.

Graft 570 may also be coated (in the case of tubular grafts, on the inside and/or outside) with other materials to further enhance their bio-utility and/or biocompatibility. Examples of suitable coatings are medicated coatings, hydrophilic coatings, smoothing coatings, collagen coatings, human cell seeding coatings, etc. For example, the artificial graft may be coated with additional biocompatible materials to minimize thrombogeneity of the graft. Coatings such as endothelial cell linings found in autologous vessels, polymers, polysaccharides, etc can provide a non-thrombogenic surface to increase endothelial cell proliferation. The graft can also be modified with one or more proteins or growth factors to increase cell adhesion, growth, and proliferation such as, for example, VEGF, FGF-2 and other HBGF (Heparin Binding Growth Factors).

Vascular Stents and Drug Eluting Coronary Stents

Vascular stents are small metallic devices which are used to keep the blood vessels open following balloon angioplasty. Examples of commercially available stents are the Multi-Link Vision™ Coronary Stent System available commercially from Guidant Corporation (Indianapolis, Ind.), and the Driver™ Coronary Stent System or BeStent2™ available commercially from Medtronic, Inc. (Minneapolis, Min.). However, it should be readily apparent that any stent may be used in the present invention.

Figure 27B:
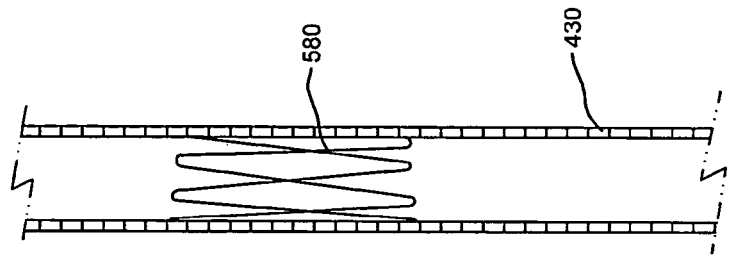
FIGS. 27A and 27B are illustrations of a stent which is expanded by balloon dilatation.
Figure 27A:
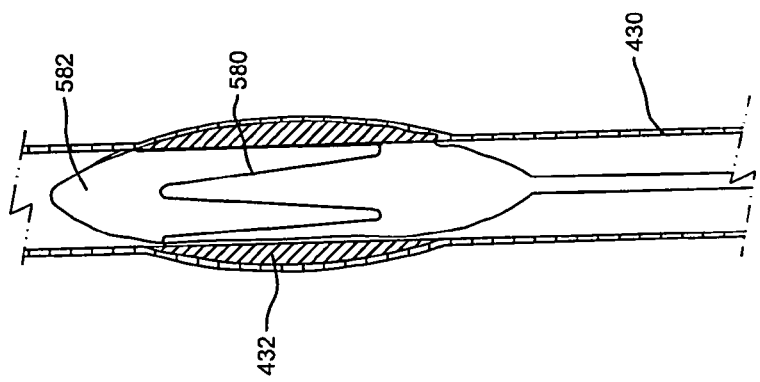

Commercially available stents can take a variety of forms. For example, one such stent 580, as shown in FIGS. 27A and 27B, is comprised of a stainless steel wire which is expanded by balloon dilatation. Stent 580 may be crimped onto a balloon 582, as shown in FIG. 27A, for delivery to an affected region of a vessel 430 such as a coronary artery. For the sake of simplicity, multiple layers of a wall of vessel 430 are shown as a single layer, although it will be understood by those skilled in the art that the lesion typically is a plaque deposit within the intima of the vessel 430.

One suitable balloon for delivery of stent 580 is the Maverick™ PTCA balloon commercially available from Boston Scientific Corporation (Natick, Mass.), although any standard or non-standard balloon may be used. Alternatively, non-balloon stents may be used (such as self-expanding stents, for example). The stent-carrying balloon 582 is then advanced to the affected area and across the lesion in a conventional manner, such as by use of a guide wire and a guide catheter. An example of a suitable guide wire is the 0.014" Forte™ manufactured by Boston Scientific Corp. and a suitable guiding catheter is the ET 0.76 lumen guide catheter.

Once balloon 582 is in place across the lesion 432, as shown in FIG. 27A, balloon 582 may be inflated in a conventional manner. In selecting a balloon, it is helpful to ensure that the balloon will provide radially uniform inflation so that stent 580 will expand equally along each of the peaks. The inflation of the balloon 582 causes the expansion of stent 580 from its crimped configuration to an expanded configuration, as shown in FIG. 27A. The amount of inflation, and commensurate amount of expansion of stent 580, may be varied as dictated by the lesion itself. Following inflation of balloon 580 and expansion of stent 580 within vessel 430, balloon 580 is deflated and removed. The exterior wall of vessel 430 returns to its original shape through elastic recoil. Stent 580, however, remains in its expanded form within the vessel, and prevents further restenosis of the vessel. The stent maintains an open passageway through vessel 430, as shown in FIG. 27B, so long as the tendency toward restenosis is not greater than the mechanical strength of stent 580.

In embodiments of the present invention, SAW of Rayleigh and/or Lamb type may be activated in several locations, including: on the delivery catheter system and stent 580, on the inner surfaces of vessel 430, between stent 580 and the delivery catheter, between an external surface of stent 580 and an internal surface of vessel 430. There may be several possibilities for actuator placement: on a portion of the inner and/or outer channel of the delivery catheter which is outside of the body, wherein frequency and attachment angle variations of the actuator will initiate SAW on the guide catheter surfaces and on stent 580; or the delivery catheter and/or the stent may be comprised of or coated with piezoelectric material and may act as an actuator. For example, a coating of PZT 5 or PZT 5H may be used. SAW may improve adhesion, friction, biointegration or other properties of the device to enhance its patency in the subject passage. Such enhanced interactivity is generally provided by providing SAW that interacts with the surface of the passage, e.g., an inner or outer wall surface, to promote integration therewith or attachment thereto. In some embodiments, actuator 200 can either be attached or incorporated to the outer or inner surface of the stent 580. The actuation frequency may be in a range of 20 KHz-50 MHz, while amplitudes of SAW may be in a range of 1-50 nanometers.

Other types of stents which may be used with the present invention include self-expanding stents, for example those made of Nitinol™, drug eluting coronary stents, such as Cordis Cypher™ sirolimus-eluting stent or the Boston Scientific Taxus™ paclitaxel-eluting stent system. Examples of the medications on the currently available stents are sirolimus and paclitaxel, as well as anti-inflammatory immunomodulators such as Dexamethasone, M-prednisolone, Interferon, Leflunomide, Tacrolimus, Mizoribine, statins, Cyclosporine, Tranilast, and Biorest; antiproliferative compounds such as Taxol, Methotrexate, Actinomycin, Angiopeptin, Vincristine, Mitomycin, RestenASE, and PCNA ribozyme; migration inhibitors such as Batimastat, Prolyl hydroxylase inhibitors, Halofuginone, C-proteinase inhibitors, and Probucol; and compounds which promote healing and re-endothelialization such as VEGF, Estradiols, antibodies, NO donors, BCP671, and the like. Sirolimus, for example, had been used previously to prevent rejection following organ transplantation. Unfortunately, the use of polymer coatings on stents can lead to thrombosis and other complications; anticoagulants are typically required at least for the first three months after placement to alleviate some of these issues.

However, the provision of SAW of Rayleigh and/or "pseudo" Rayleigh and/or Lamb type on drug-eluting stents can eliminate the need for such polymer coatings and thus minimize some of these complications. SAW may also provide better drug release. Moreover, the use of SAW may provide improved fluid dynamics by creation of a hydrophobic surface, improvement of drug elution, improvement of tissue response to the drug, and creation of a hydrophobic surface on the inner surface of stent 580.

The methods and systems of the present invention may also include the use of SAW of Rayleigh and/or "pseudo" Rayleigh and/or Lamb types with other types of stents such as, for example, urethral and biliary stents. In these body lumens, it may be desirable to prevent crystallization on the struts of the stents. In the biliary tree, for example, bilirubin crystals deposit on foreign surfaces such as sutures and permanent or temporary stents. Such deposition typically decreases the useful life of the stents and can require patients to undergo multiple procedures for successful therapies. A similar situation exists in the urinary tract. Uric acid precipitates on stents and leads to "stent encrustation," which ultimately leads to device failure. SAW application to these types of stents may provide super hydrophobic features which would resist crystal formation due to an aqueous phase interfacing between the stent surface and the crystal inducing elements, thereby preventing deposit of crystal elements thereon.

Figure 28A:
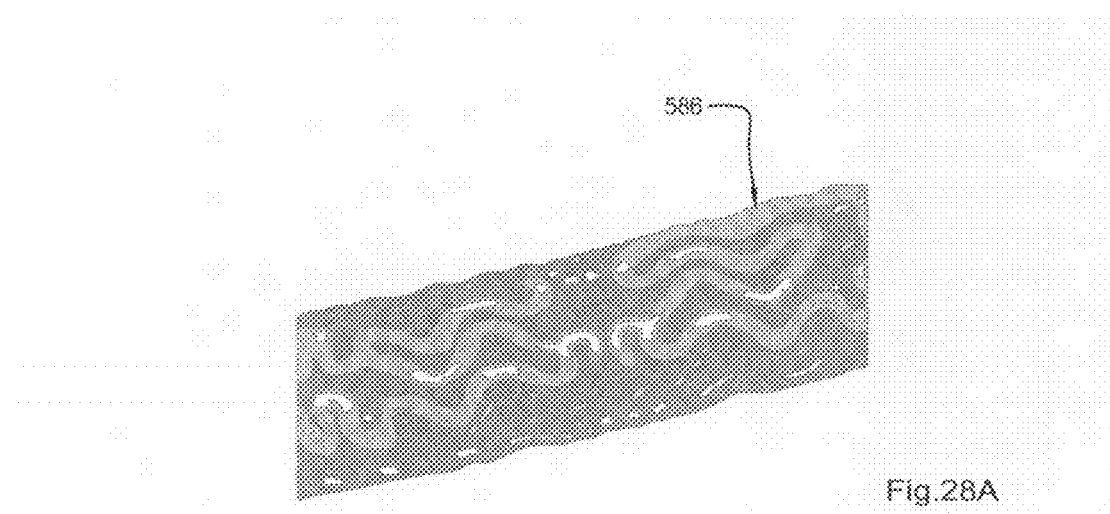
FIG. 28A is an illustration of a stent.
Figure 28B:
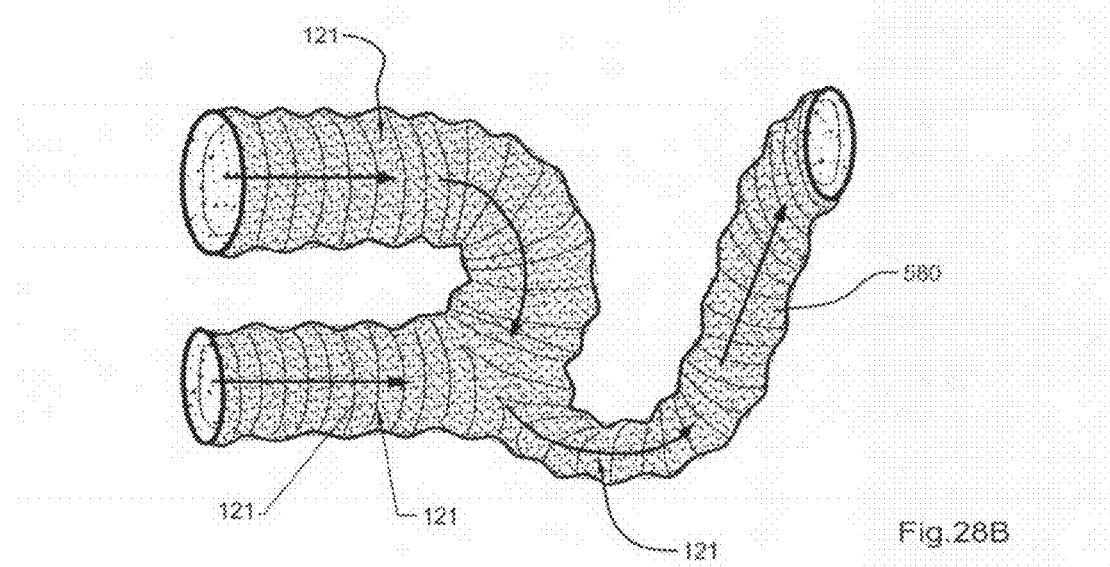
FIG. 28B is an illustration of an enlarged portion of the stent of FIG. 28A, wherein a single strut of the stent is visible.

Reference is now made to FIG. 28A, which is an illustration of a stent 580, and FIG. 28B, which is an illustration of an enlarged portion of stent 580, wherein a single strut of stent 580 is visible. As shown in FIG. 28B, SAW may be produced in various directions. SAW may surround an entire surface, including surfaces at varying angles and of varying shapes, as shown.

Figure 29:
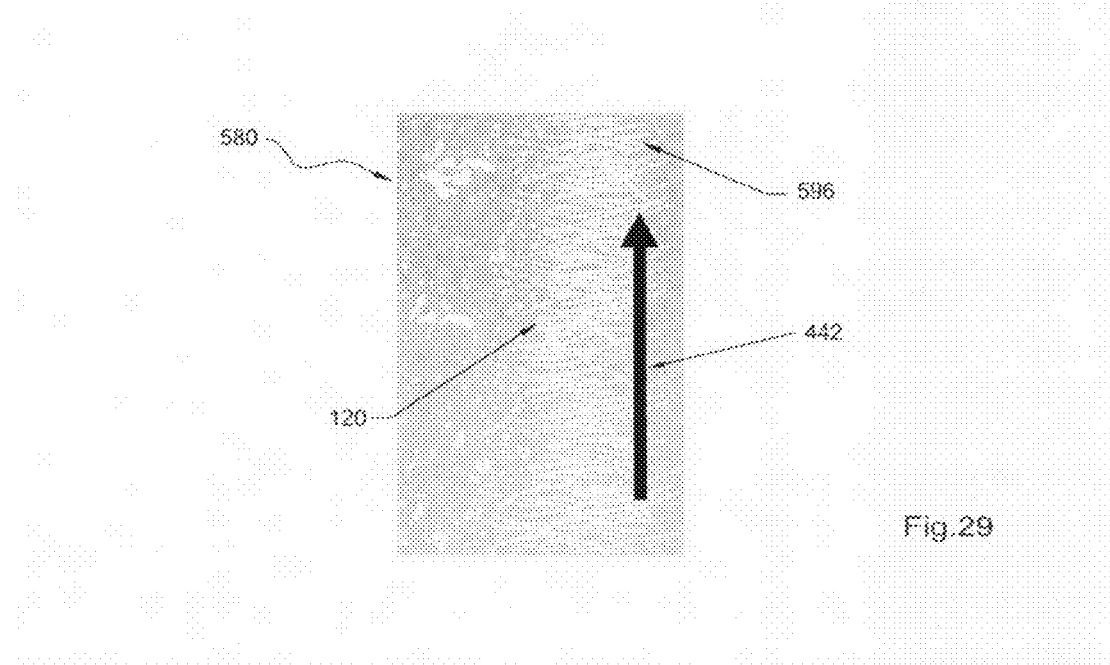
FIG. 29 is an illustration of a stent comprised of piezoelectric material wherein an internal surface of the stent has a fibrous structure.

In some embodiments, as shown in FIG. 29, stent 580 is comprised of piezoelectric material wherein an internal surface 120 surface of stent 580 has a fibrous structure 596, which may be comprised of piezoelectric material or may be any other non-piezoelectric material. The fibrous structure is in direct contact with flowing blood, shown by arrow 442. In this embodiment, direct and reverse piezo effects may be applied simultaneously to separate parts of stent 580. The blood flow kinetic energy is used as an energy source for piezo-electric excitation. The frequency of blood pulsation is about 1-3 Hz and is too low for SAW excitation, which requires KHz range frequency. As shown in FIG. 29, part of the stent is manufactured from a piezo-electric material, such as PZT 5, PZT 5H, PZT 4 or PZT 8. Fibers of fibrous structure 596 have different lengths and thicknesses. Thus, when the fibers contact flowing blood, which pulsate in low frequency, the fibers will vibrate in different regimes creating a wide spectrum of electrical signals in the piezo-electric material. The spectrum of electrical potential may reach the ranges between 10 Hz-10 MHz. The frequency of 0.1 MHz to 10 MHz may excite SAW in the piezo-electric material of the stent. The SAW on the outer surface of the stent will have a therapeutic effect on tissue, and on the inner surface will prevent crystallization, due to the relative velocities which particles obtain due to the SAW.

Figure 30:
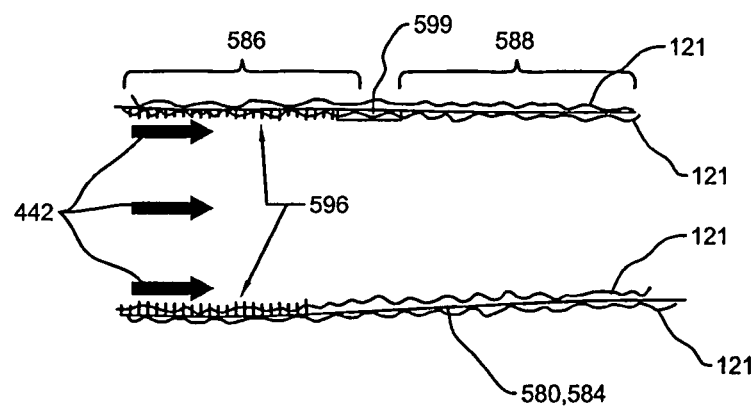
FIG. 30 is an illustration of a two-part piezoelectric stent, in accordance with embodiments of the present invention.

Reference is now made to FIG. 30, which is an illustration of a two-part piezoelectric stent 584. Piezoelectric stent 584 has a receiving portion 586 and a transmitting portion 588. Receiving portion 586 causes a direct piezoelectric effect on transmitting portion 588, and transmitting portion 588 is configured to transmit SAW 121 on the entire length of stent 584. Receiving portion 586 and transmitting portion 588 are electrically connected to one another. The flow of blood, depicted by arrows 442, causes a piezoelectric effect in fibrous portion 596 (which comprised of piezo-fibers) of stent 584. Since piezo-fibers of fibrous portion 596 have varying geometries and piezo-coefficients, blood flow can create self-vibrations in some of these fibers, which leads to vibrations in others of the fibers. As a result, a wide spectrum of electrical potential is created in the material. This potential is accumulated into a microprocessor 599, which may act as a high frequency filter, which transmits electrical energy received from receiving portion 586 to transmitting portion 588. The transmitted electrical energy is in the form of an electrical signal of required frequency, which is proportional to SAW wave length. The electrical signal enters transmitting portion 588 and due to the reverse piezo effect, SAW of Rayleigh and/or "pseudo" Rayleigh, and/or Lamb type are produced. SAW are transmitted through external and internal stent surfaces and effect the receiving portion 586. The action has a closed loop, wherein the energy is accumulated from blood flow and transferred to excite SAW of Rayleigh and/or "pseudo" Rayleigh, and/or Lamb type, as described. The stent may have several receiving and/or transmitting portions, which may be configured in the entire stent in a parallel or perpendicular manner with respect to the blood flow direction. Additionally, they may occupy equal or different areas of the stent. The embodiment of self excited vascular stent may be applied to any other implant, wherein SAW excitement is desired.

Occlusion of Blood Vessels in the Brain and Other Organs of the Body

SAW can be used in the treatment of various diseases and conditions of the circulatory system and other organs of the body that are beneficially treated by the occlusion of blood vessels. Examples of the numerous diseases that can be treated by blocking associated blood vessels using, for example, intravascular coils, beads, synthetic grafts or other liquid embolic agents include arteriovenous (AV) fistulas, AV malformations, aneurysms and pseudoaneurysms, patent ductus arteriosus, patent foramen ovale, gastrointestinal bleeding, renal and pelvic bleeding, and tumors.

Placement of various substances (e.g., a liquid adhesive such as isobutylcyanoacrylate (IBCA)) within the blood vessels is one of the methods of encouraging the formation of thrombus (clot) which leads to the complete occlusion of the vessels. Occlusive coils have also been used to occlude blood vessels. The purpose of the coil is to encourage quick formation of a thrombus around the coil.

Of the many diseases that may be treated with embolic coils, cerebral aneurysms are of particular interest. Ruptured and unruptured cerebral aneurysms may in some cases be treated by a surgical approach in which the aneurysm is visualized directly and then surgically clipped thereby blocking blood flow into the aneurysm. Once the aneurysm is eliminated from the blood flow the risk of hemorrhage is eliminated. Another less invasive approach to the treatment of cerebral aneurysms is an endovascular approach, in which a catheter is introduced into the cerebral vascular system from a peripheral access point, such as a femoral artery, to access the aneurysm internally. The catheters can be used to deliver embolic devices, such as a balloon or a coil, to the site of the aneurysm to block blood flow into the aneurysm. The use of embolic coils, however, can lead to complications because the coils can compact over time and allow re-filling of the aneurysm, posing risk of rupture.

The present embodiment of the invention involves the use of an endoluminal patch for the repair of, for example, side wall aneurysms in the brain or elsewhere in the arterial vasculature. Although the present methods are discussed in relation to the treatment of cerebral side wall aneurysms in particular, it is to be appreciated that the systems and methods of the present invention may be used in connection with a variety of other embolotherapy procedures in various blood vessels and organs of the body where an embolic device, such as a coil or embolic patch material, may be deployed.

An endoluminal patch is mounted on a compliant, low-pressure balloon catheter. These procedures use catheters introduced into the cerebral vascular system from a peripheral access point, e.g. a femoral artery, to access the aneurysm internally. The catheter is used to deliver the patch to the site of the aneurysm to block blood flow into the aneurysm. The embolic delivery catheter is introduced into a blood vessel in the brain having a side wall aneurysm or other disease condition therein. The diseased site may be an aneurysm or a fistula, AV malformation, or other disease in which deployment at, on or near the disease condition would result in reduced or stopped flow to the abnormal area. The endoluminal patch is placed via the delivery catheter over the aneurysm neck to block blood from entering the aneurysm. The catheter is typically introduced into the cerebral vasculature system of the patient from a peripheral access point such as a femoral artery and guided with the aid of fluoroscopy to the brain through the aorta and through one of the carotid (or vertebral) arteries in the neck. Once the insertion catheter and the patch are threaded through the vasculature system to the site of the aneurysm in the brain, the patch is aligned with the aneurysm neck under radioscopic guidance. The patch is applied to the vessel wall by dilating the balloon catheter to press-fit the patch onto the vessel wall.

In one embodiment, the actuator is placed on a neck area directly over the Adam's Apple. The attachment of the actuator is made sufficiently firm to create pressure between the actuator and the cricoid cartilage forming the Adam's Apple. The vibrations are then delivered through cerebral vasculature system to the patch, actuating the surfaces and inhibiting healing. The patch with a miniature actuator/sensor is another possibility of SAW employment for brain disease treatment. SAW can also be adapted to enhance the effects of chemotherapy by opening up the blood-brain barrier, which insulates the brain from foreign substances but also prevents many drugs from reaching diseased tissue there.

Sutureless Graft Prostheses

The methods, devices and systems of the invention generally described above may also be used in the performance of anastomosis of blood vessels, ducts, lumens or other tubular organs, e.g., for sutureless anastomosis procedures in which one vessel is joined to another vessel without the use of sutures.

Arterial bypass surgery is a common modality for the treatment of occlusive vascular disease. Such surgery typically involves an incision and exposure of the occluded vessel followed by the joiner of a graft, e.g., a mammary artery, saphenous vein, or synthetic graft (all collectively referred to hereinafter as the "bypass graft"), to the occluded vessel (hereinafter the "native" blood vessel distally (downstream) of the occlusion. The upstream or proximal end of the bypass graft is secured to a suitable blood vessel upstream of the occlusion, e.g., the aorta, to divert the flow of blood around the blockage. Other occluded or diseased blood vessels, such as the carotid artery, may be similarly treated. Moreover, similar procedures are conducted to place a graft between an artery and a vein in dialysis patients.

Current methods available for creating an anastomosis include hand suturing the vessels together. Suturing the anastomosis is time-consuming and often does not provide a leak-free seal and can lead to a site of turbulent blood flow on occlusion. Thus, it is desirable to reduce the difficulty of creating the vascular anastomosis and provide a rapid method for making a reliable anastomosis between a graft vessel and artery.

One method currently available involves the use of stapling devices. These instruments are not easily adaptable for use in vascular anastomosis. It is often difficult to manipulate these devices through the vessels without inadvertently piercing a side wall of the vessel. In addition to being difficult to operate, these devices often do not provide a reliable leak-free seal.

Figure 31A:
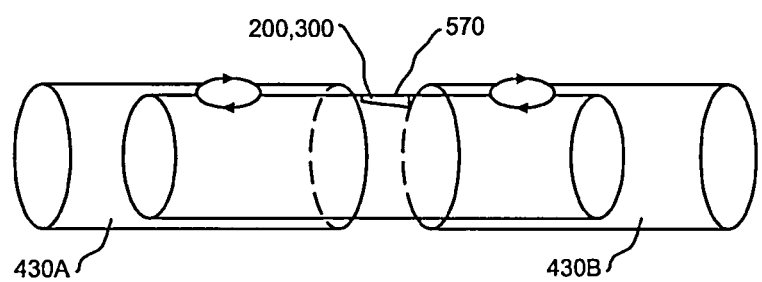
FIG. 31A is an illustration of a coupled first vessel and second vessel in an end-to-end anastomosis.
Figure 31B:
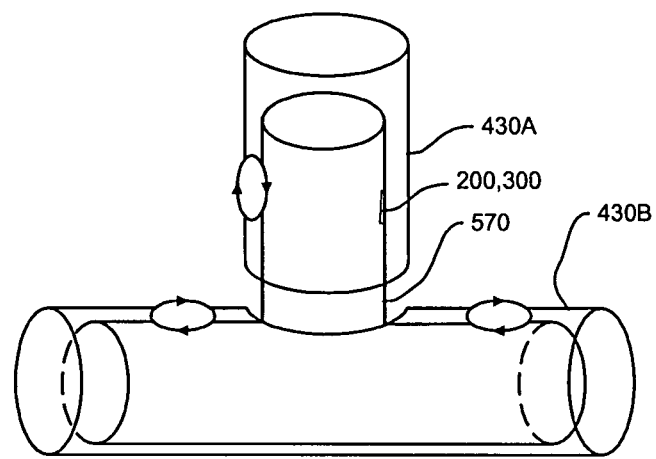
FIG. 31B is an illustration of graft having a T-shape configuration for treating an end-to-side anastomosis.

The present embodiment of the invention involves improvements to conventional devices and methods for performing vascular anastomoses. The invention facilitates positioning one vessel in the fluid path of another vessel to enhance the fluid flow juncture there between. The invention provides artificial graft tubing by which anatomical structures, such as blood vessels, fallopian tubes, intestine, bowel, ureters, and outer nerve sheaths are anastomosed, preferably without the use of sutures. The new tubing may be artificial graft tubing in the form of a simple tube (as shown in FIG. 31A, for example), or a T-tube as shown in FIG. 31B for example, or any other suitable tubing shape or configuration. Alternatively, the new tubing may be a combination of artificial and natural tubing (e.g., natural tubing disposed substantially concentrically inside artificial tubing).

The artificial tubing may be made from any suitable biocompatible material including, for example, a flexible, semi-porous metal mesh (e.g., Nitinol mesh, stainless steel mesh, titanium mesh and the like), treated natural tissue, laboratory-engineered tissue, and synthetic polymer fabrics or other polymeric material such as Dacrong, PTFE, polyimide mesh, ceramic, glass fabrics and the like and may be covered with or comprised of piezo-electric material.

The present embodiment of the invention entails the use of SAW on the surface of graft to enhance the interaction of the tubing with the passages in which it is used. SAW are employed to improve adhesion, friction, bio-integration or other properties of the device to enhance its patency in the subject passage.

The artificial grafts of this invention may be coated with other materials to still further enhance their bio-utility and/or biocompatibility. Examples of suitable coatings are medicated coatings, hydrophilic coatings, smoothing coatings, collagen coatings, human cell seeding coatings, etc. The SAW activation on the graft helps the graft to retain these coatings. For example, the graft tubings may be coated with additional biocompatible materials to minimize thrombogeneity of the tubing. Coatings such as endothelial cell linings found in autologous vessels, polymers, polysaccharides, etc can provide non-thrombogenic features to increase endothelial cell proliferation. The tubing material can also be modified with one or more proteins or growth factors to increase cell adhesion, growth, and proliferation such as, for example, VEGF, FGF-2 and other HBGF (Heparin Binding Growth Factors).

The SAW actuator on the inside and/or outside diameter of the tubing will allow a firm press-fit into the inner (or outer) diameter of the native host vessel or to connect other synthetic graft vessels.

Reference is now made to FIG. 31A, which is an illustration of a coupled first vessel 430A and second vessel 430B in an end-to-end anastomosis. An artificial graft 570 with an actuator 200 and processor 300 incorporated into or attached to graft 570 is inserted into an opening in a bypass graft vessel (which can include a natural or synthetic graft vessel) and a native vessel to be connected. At least a portion of graft 570 is radially expanded (e.g., with the use of a balloon catheter, for example) to sealingly press-fit and secure the tubular graft 570 to the inner wall of the vessels 430. Graft 570 is sufficiently rigid to substantially its preformed configuration after expansion. Graft 570 may be radially self-expandable to a pre-formed configuration (e.g., via the use of a shape memory alloy for the tubing such as Nitinol, for example), and thus may assume a press-fit configuration within the vessels to sealingly join them without the use of an access device such as a balloon catheter. Reference is now made to FIG. 31B, which is an illustration of graft 570 having a T-shape configuration for treating an end-to-side anastomosis, in accordance with other embodiments of the present invention. Graft 570 is secured to an opening in a side wall of the vessel 430. Although grafts in the form of tubing are described above, certain aspects of the invention are equally applicable to other graft procedures and to grafts having virtually any cross-sectional shape depending upon the desired application, including, e.g., circular, elliptical, polygonal, e.g., square, rectangular, pentagonal, hexagonal, octagonal, trapezoidal, rhomboid, etc. Further, it will be appreciated that the cross-sectional shape of the body structure of the graft may be the same as or different from the cross-sectional shape of the vessel into which it is inserted, depending upon a number of factors, including, e.g., the method used to fabricate the graft, and/or its desired application.

Applying the methods described here above, SAW may be achieved on the tubular grafts for short or long periods, as desired. An actuator 200 may be incorporated into the graft, or the graft 570 may be comprised of piezo materials. SAW improves adhesion, friction, bio-integration or other properties of the device to enhance its patency in the subject vessel.

Orthopedic Implants

SAW incorporated into or onto orthopedic implants can improve biocompatibility, infection resistance, bone integration, prevention of unwanted cell growth, and durability of those implants when used in and around orthopedic tissues, such as bone, ligaments, muscles, etc. Examples of orthopedic implants that can benefit from SAW enhanced surfaces include without limitation total knee joints, total hip joints, ankle, elbow, wrist, and shoulder implants including those replacing or augmenting cartilage, long bone implants such as for fracture repair and external fixation of tibia, fibula, femur, radius, and ulna, spinal implants including fixation and fusion devices, maxillofacial implants including cranial bone fixation devices, artificial bone replacements, dental implants, orthopedic cements and glues comprised of polymers, resins, metals, alloys, plastics and combinations thereof, nails, screws, plates, fixator devices, wires and pins and the like that are used in such implants, and other orthopedic implant structures as would be known to those of ordinary skill in the art.

Reference is now made to FIGS. 32A and 32B, which are illustrations of an orthopedic implant 610 in the form of a hip stem 612, having a substrate 611 and a porous layer 614. Porous layer 614 can include beads, fibers, wire mesh and other known materials and shapes thereof used to form porous layer 614. In some embodiments, porous layer 614 includes piezoelectric fibers. Actuator 200 and processor 300 are incorporated into implant 610. In particular, the present embodiment of the invention provides such orthopedic implantable devices with SAW actuators to enhance the interaction of the implants with the tissues, joints, cartilage, bones, and other bodily structures with which they make contact at the implantation site. SAW on the surface of implants can enhance bone growth reaction at the implant site by encouraging and enhancing proliferation of osteoblasts, versus fibroblasts and other undesirable cells. Enhanced bone growth activity encourages good fixation of the implant over time and prevents loosening due to fibroblastic response. In addition, SAW on orthopedic implants can prevent infection at the implant site, e.g., by preventing the growth of bacteria and other infectious organisms such as viruses and fungus.

Alternatively, or additionally, the SAW can be made from piezoelectric materials, and SAW can be used to enhance the durability and resistance to wear that occurs in a load bearing implantation site, thereby preventing micro degradation and resultant debris in the joints.

The implants of this invention may also be coated on the inside and/or outside with other materials to still further enhance their bio-utility and/or biocompatibility.

Pacemaker infection caused by bacteria suggests that early removal of the entire system is needed if infection is to be controlled. Otherwise, bacteremia usually reappears, and this reappearance carries a poor prognosis, even with long-term antibiotic therapy, unless the pacemaker is removed. Pacemakers with SAW actuators incorporated into their design may be desirable and effective against bacteria infection.

It should be readily apparent that parameters are determined based on the type of device and desired effect. For example, an orthopedic implant, which is relatively large and covers a large surface area as compared to other devices such as stents or grafts, will require higher energy inputs in order to arrive at satisfactory surface acoustic wave parameters.

4. Other Positive Reactions Optionally May be Achieved:

1. Prevention of attachment of particulate of matter to heart valves (artificial and natural) vascular bed and surfaces—peritoneum fascia pleura, pericard, sinovia—epithelia, endothelial connective or any other surface which surrounds and protects the nervous system.

2. Movement of stagnating fluids which arises as a result of shock of various etiologies and impairs the microcirculation. Vibrations improve gas exchanges and the maintenance of the homeostasis.

3. The surface area is dynamically "increased" resulting in increased gas, nutrients, fluid and heat exchange.

4. Inhibition of adhesion formation following surgery through specific targeted vibrations to affected area.

5. Clearing and draining of fluid along surfaces by using vibrations.

6. Improvement of flow in thin tubes through decreased friction (boundary layer effect)

7. Tropic effect upon selected structures or areas due to stimulation and micromotion of cells and lining of organs again through enhanced exchanges of oxygen, nutrients and disposal of waste material.

8. Stimulation of muscles of sphincters such as anal gastric or urinary, intended to strengthen the sphincter or as a treatment of stress incontinence or reflux of acid from the stomach to the esophagus incontinence.

9. Resistance of crystallization, resistance of formation of thrombus, resistance of tissue in-growth due to obtained hydrophobic properties.

10. Interaction of biomaterials and SAW

As also will be appreciated by those of skill in the art, many aspects of the current invention are optionally variable (e.g., surface chemistries on the surfaces treated with SAW, etc.). Specific illustration of various modifications, etc. herein, should therefore not be taken as limiting the current invention.

According to some embodiments of the present invention, by means of applying combinations of mechanical vibrations and various techniques for their propagation, we create on internal, external and torsion surface of medical device nanovibrations of very small amplitude and pressure. This is novel antibacterial coating, so-called "nanovibration coating". The magnitude of nanovibrations is several/or ten times smaller in comparison to the size of bacteria and such small vibrations do not increase temperature. It is possible to control magnitude, direction, and rate of nanovibrations on external and internal surfaces of medical device. It is possible to create at the same time propagation of elastic waves of different types (different harmonics and directions). This allows creation of spacious nano elastic waves on internal, external and torsion surfaces of medical device.

EXAMPLES

In-vitro tests were conducted with suspensions of *Escherichia coli*, *Enterococcus faecalis*, *Candida albicans*, *Enterobacter aerogenes*, *Staphylococcus epidermidis*, *Streptococcus mitis*, *Proteus mirabilis*, *Psuedomonas aeruginosa*, *Klebsiella pneumonia* and *Citrobacter freundii*. These bacteria most commonly develop clinically relevant biofilms.

Three centimeter sections were sliced from each catheter; one was subjected to sonication at 20 KHz, 3-4 Watt for 2×30 sec. to shed the biofilm off the catheter and disperse it in the solution. Bacterial bioburden which developed on the surfaces of the SAW-treated catheters were compared to control catheters by titration. As shown in Table 1, reductions of an average of $1.62 \pm 0.67 \log_{10}$ in bacterial biofilms were found on surfaces of SAW treated catheters relative to controls.

TABLE 1

Bacterial bioburden (CFU/ml) on 16 Fr Foley catheters attached with piezo elements generating SAW. Titers correspond to overall bacterial load on the 3 cm sections of catheters.

| Bacterial species | Control | SAW treated | Log Reduction |
|---|---|---|---|
| Escherichia coli | $2.2 \times 10^6$ | $2.4 \times 10^5$ | −0.96 |
| Enterococcus faecalis | $2.6 \times 10^6$ | $2.8 \times 10^5$ | −0.97 |
| Candida albicans | $1.0 \times 10^6$ | $5.9 \times 10^4$ | −1.23 |
| Pseudomonas aeruginosa | $1.7 \times 10^7$ | $1.4 \times 10^5$ | −2.1 |
| Proteus mirabilis | $3.8 \times 10^6$ | $3.6 \times 10^5$ | −1.02 |
| Enterobacter aerogenes | $4.3 \times 10^7$ | $2.1 \times 10^6$ | −1.31 |
| Citrobacter freundii | $5.4 \times 10^8$ | $9.8 \times 10^5$ | −2.74 |
| Klebsiella pneunomiae | $9.5 \times 10^6$ | $7.3 \times 10^5$ | −1.11 |
| Providencia alcalifaciens | $6.5 \times 10^5$ | $1.0 \times 10^4$ | −1.81 |
| Staphylococcus epidermidis | $6.9 \times 10^4$ | $9.5 \times 10^2$ | −1.86 |
| Streptococcus mitis | $1.0 \times 10^6$ | $2.1 \times 10^3$ | −2.68 |

Figure 33:
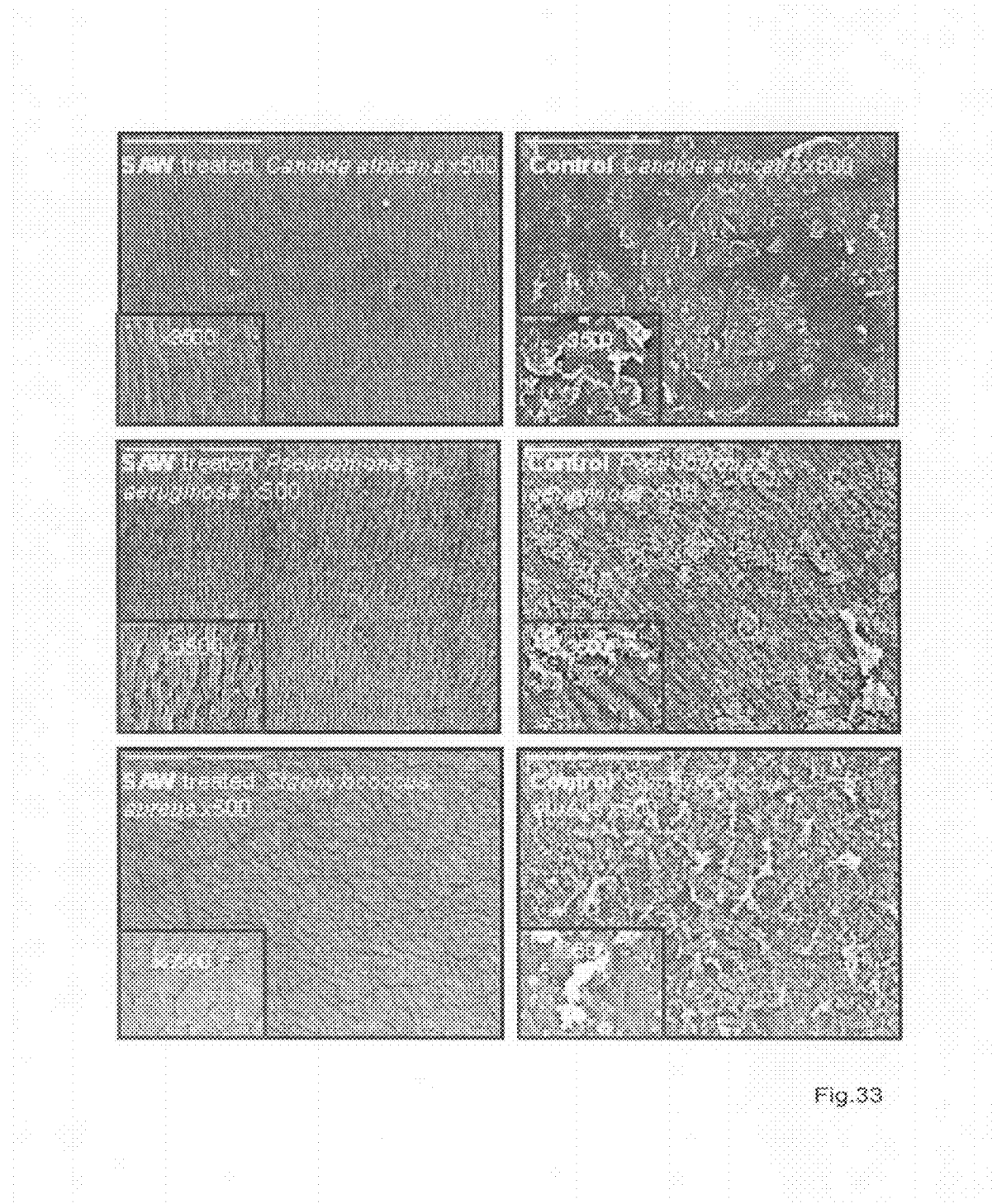
FIG. 33 is an illustration of results of scanning electron microscopic analysis of treated and untreated catheters.

Other segments of these catheters were subjected to scanning electron microscopic analyses the results of which are shown in FIG. 33. Photos of bacterial biofilm development on 16 Fr urinary catheter body segments following flow of bacteria through the catheter in vitro are depicted. Comparison of catheters treated with surface acoustic nanowaves from an actuator attached to the catheters shows marked reductions in biofilm formation with catheters virtually clean of any visible adherent microbes. These results are evident in the SAW treated urinary catheters irrespective of the type of bacterium that was examined. Similar reductions in biofilm burden were obtained on glass surfaces glued with piezo actuators (data not shown), indicating that the piezo element-generated elastic waves can be adjusted to prevent microbial biofilm formation on different types of surfaces varying in consistency and shapes. Thus, it can be concluded that surface acoustic nanowaves interfere with adhesion of planktonic bacteria to solid surfaces. These studies of mechanisms by which SAW prevent bacterial biofilm formation on solid surfaces focused on whether the ultrasonic energy prevents adhesion of planktonic bacteria to solid substrates, the first step in the biofilm formation process.

In-vivo tests were conducted to test whether prevention of microbial biofilm formation on catheters with attached acoustic nanowave actuators can be seen in an animal model. We inserted 10 Fr Foley catheters to which a piezo actuator was attached at the extracorporeal portion of the catheter into the urinary bladders of male rabbits in a sterile manner. The actuators were activated in four of eight tested rabbits (in three separate experiments) for up to 9 days. Urine samples were collected daily, bacterial load quantified and time to bacteriuria determined. Upon termination of the experiments the animals were sacrificed, the bladder and urethra opened, the catheters removed and biofilm content examined by scanning electron microscopy. As shown in Table 2, urine from rabbits in which the catheters were treated with SAW remained sterile for 5, 7 and 9 days, (26 cumulative days of sterile urine) despite the extensive contamination of the perianal area with feces. Furthermore, the bacteriuria which did develop in these rabbits was mostly of low titers, whereas 3 of 4 control rabbits developed bacteriuria of $>10^6$ CFU/ml within 2-3 days. The fourth control rabbit developed bacterial titres of $>10^8$ CFU/ml on day seven.

TABLE 2

Time to bacteriuria in rabbits inserted with 8 Fr. Foley catheters to which SAW-generating piezo actuators have been attached at the extracorporeal catheter body.

| | Bacterial titer | | | | | | | | |
|---|---|---|---|---|---|---|---|---|---|
| Rabbit No. | Day 1 | Day 2 | Day 3 | Day 4 | Day 5 | Day 6 | Day 7 | Day 8 | Day 9 |
| 163-A | 0 | 0 | 0 | 0 | 0 | 0 | 0 | — | — |
| 229-A | 0 | 0 | 0 | 0 | 0 | 0 | 0 | 0 | 0 |
| 265-A | 0 | 0 | 0 | 0 | 0 | $10^4$ | $10^6$ | — | — |

TABLE 2-continued

Time to bacteriuria in rabbits inserted with 8 Fr. Foley catheters to which SAW-generating piezo actuators have been attached at the extracorporeal catheter body.

| Rabbit No. | Bacterial titer | | | | | | | | |
|---|---|---|---|---|---|---|---|---|---|
| | Day 1 | Day 2 | Day 3 | Day 4 | Day 5 | Day 6 | Day 7 | Day 8 | Day 9 |
| 143-A | 0 | 0 | 0 | 0 | 0 | $3 \times 10^3$ | $2 \times 10^4$ | — | — |
| 28-C | 0 | $1.4 \times 10^7$ | $5 \times 10^7$ | — | — | — | — | — | — |
| 31-C | 4 | $10^4$ | $5 \times 10^3$ | $10^4$ | 0 | 0 | $8 \times 10^8$ | $2.5 \times 10^8$ | — |
| 150-C | 0 | 6 | $4 \times 10^6$ | $10^8$ | — | — | — | — | — |
| 144-C | 70 | $10^6$ | $5 \times 10^6$ | — | — | — | — | — | — |

Bacteria concentration values are calculated by CFU/ml
A—SAW treated, C—Control.

The average number of days to development of urinary tract infection, defined as bacteriuria of $>10^5$ CFU/ml, is summarized in FIG. 34.

Figure 35A:
FIGS. 35A and 35B are illustration of results of scanning electron microscopic analysis performed on the internal surfaces of recovered catheters.
Figure 35B:
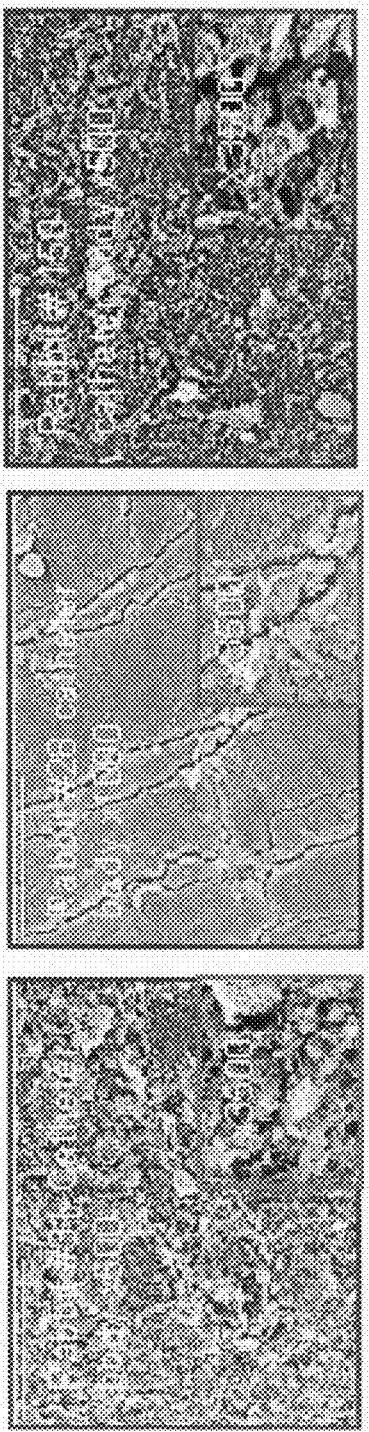

Scanning electron microscopic analyses performed on the internal surfaces of recovered catheters reveal absence of bacterial biofilms on surfaces of catheters treated with piezo element-generated SAW as shown in FIG. 35A. In contrast control group catheters were found to be covered with varying densities of microbial biofilms as shown in FIG. 35B).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method for treatment of a surface of an indwelling medical device to prevent attachment of bacteria thereto, the method comprising:
    providing an actuator for producing surface acoustic waves (SAW) on a surface of the medical device and a processor for controlling parameters of said actuator;
    producing elliptical motion of particles on the surface of the medical device by activating said actuator and thereby producing said SAW, wherein said elliptical motion causes vibration of bacteria on the surface of the medical device at a particular vibration amplitude relative to vibration of the surface of the medical device; and
    controlling parameters of said actuator via said processor such that the vibration amplitude of the bacteria is smaller than a Z-potential repulsive zone of the surface of the medical device,
    such that said SAW inhibit attachment of bacteria to the surface of the medical device.

2. The method of claim 1, wherein said providing comprises providing a piezoelectric actuator.

3. The method of claim 2, wherein said actuator comprises a fibrous material comprising fibers having different lengths and thicknesses, wherein said fibers may create a wide range of electrical potentials when subjected to low frequency of body movements, wherein said electrical potentials may create surface acoustic waves on said device.

4. The method of claim 3, wherein said body movements are selected from the group consisting of: blood flow, heart pumping and limb movement.

5. The method of claim 1, wherein said providing comprises providing an electromagnetic actuator.

6. The method of claim 1, wherein said providing comprises providing laser pulses.

7. The method of claim 1, wherein said producing said SAW comprises producing waves selected from the group consisting of: Rayleigh waves, "pseudo" Rayleigh waves, and Lamb waves.

8. The method of claim 1, wherein said producing elliptical motion comprises producing elliptical motion on an external surface of the device.

9. The method of claim 1, wherein said producing elliptical motion comprises producing elliptical motion on an internal surface of the device.

10. The method of claim 1, wherein said producing elliptical motion comprises producing elliptical motion in multiple directions.

11. The method of claim 10, wherein said producing elliptical motion comprises producing elliptical motion in multiple directions simultaneously.

12. The method of claim 1, wherein said producing said SAW comprises producing waves with a spectrum plot in a range of 0.01-10 MHz.

13. The method of claim 1, wherein said producing said SAW comprises producing waves with amplitudes in a range of 1-50 nanometers.

14. The method of claim 1, wherein said medical device is selected from the group consisting of: a catheter, a stent, a graft, an orthopedic implant, an intracorporeal device, an extracorporeal device, a temporary implant, a permanent implant, a stent, a vascular graft, an anastomotic device, an aneurysm repair device, an endoscope and an embolic device.

15. The method of claim 1, further comprising providing a biologically compatible or bioactive coating to a surface of the medical device.

16. The method of claim 1, wherein said step of providing an actuator further comprises integrating said actuator into a pad to produce said SAW and simultaneously excite longitudinal and transverse vibrations to provide conventional ultrasound to the medical device to enhance disruption of bacterial adhesion.

17. The method of claim 1, wherein said controlling parameters comprises controlling a frequency of activation.

18. The method of claim 1, wherein said controlling parameters comprises controlling a vibration mode.

19. The method of claim 1, wherein said controlling parameters comprises providing a sensor for sensing parameters related to results from said SAW, sending data from said sensed parameters to said processor, and adjusting said controlled parameters based on said sent data.

20. The method of claim 19, wherein said adjusting is done automatically in a feedback loop.

21. The method of claim 1, wherein said providing said actuator comprises positioning said actuator on the device.

22. The method of claim 1, wherein the device is comprised of piezoelectric material and wherein said providing said actuator comprises providing the device.

23. The method of claim 1, wherein said actuator comprises multiple actuators and wherein said multiple actuators are configured to provide SAW in multiple directions.

24. The method of claim 23, wherein said multiple directions provide a focused effect.

25. The method of claim 24, wherein said focused effect results in destruction of tumor cells.

26. The method of claim 1, wherein said producing elliptical motion of surface particles causes bacteria and other particles on the surface of the device to move in a direction which is opposite to a direction of surface acoustic wave propagation.

27. The method of claim 1, wherein said controlling parameters comprises providing a single phase vibration mode for reducing biofilm.

28. The method of claim 1, wherein said controlling parameters comprises providing a dual-phase vibration mode during insertion of the device into a body.

29. The method of claim 1, wherein said controlling parameters comprises providing a multi-phase vibration mode during retrieval of the device from the body.

30. The method of claim 1, further comprising providing a drug at a site of the device and wherein said producing elliptical motion of particles results in increased efficacy of the drug.

31. The method of claim 1, wherein said producing elliptical motion of particles results in a condition selected from the group consisting of: wound healing, non-sticking, elimination of encrusted biological materials, increased repair and healing, improved blood flow, reduced thrombosis, and lowered pain.

32. The method of claim 1, wherein said controlling parameters comprises combining two vibration modes and producing waves up to 1.0 MHz in frequency.

33. The method of claim 32, wherein said combining two vibration modes comprises vibrations of different harmonics within one actuator.

34. The method of claim 1, wherein said producing SAW on medical device surface results in friction reduction due to decreased contact time between device surface and tissue.

35. A method for providing surface acoustic waves (SAW) to a medical device, the method comprising:
providing a medical device, an actuator positioned on said medical device, and a processor in electrical communication with said actuator, wherein said actuator comprises a fibrous material comprising fibers having different lengths and thicknesses, wherein said fibers may create a wide range of electrical potentials when subjected to low frequency of body movements;
positioning said medical device in a body;
powering said processor through said body movements; and
activating said actuator by said powered processor,
wherein said electrical potentials may create surface acoustic waves on said device.

36. The method of claim 35, wherein said medical device is at least partly comprised of piezoelectric material, and wherein said piezoelectric material is configured to convert said body movements into electrical energy.

37. The method of claim 35, wherein said body movements are selected from the group consisting of: blood flow, heart pumping and limb movement.

38. The method of claim 35, wherein said processor comprises a power supply, a controller and an oscillator.

39. The method of claim 35, wherein said providing a medical device comprises providing an implant.

40. The method of claim 39, wherein said providing an implant further comprises providing a bioactive coating on said implant, and wherein said activating enhances activity of said bioactive coating.

41. The method of claim 39, wherein said providing an implant comprises providing a stent.

42. The method of claim 41, wherein the stent is comprised of a non-piezoelectric material and a piezoelectric material, and wherein said piezoelectric material is coated onto said non-piezoelectric material, wherein said activating comprises activating said piezoelectric material.

43. The method of claim 41, wherein said providing a stent further comprises providing a drug coating and wherein said activating enhances activity of said drug coating.

44. The method of claim 39, wherein said providing an implant comprises providing a graft.

45. The method of claim 39, wherein said providing an implant comprises providing an orthopedic implant.

46. The method of claim 39, wherein said providing an implant comprises providing a mechanical heart valve.

47. The method of claim 35, further comprising adjusting parameters of said activating based on received electrical signals.

48. The method of claim 47, wherein said adjusting parameters comprises adjusting a frequency of activation.

49. The method of claim 47, wherein said adjusting parameters comprises adjusting a vibration mode.

50. The method of claim 47, wherein said adjusting parameters comprises providing a sensor for sensing parameters of said SAW, sending data from said sensed parameters to said processor, and adjusting said controlled parameters based on said sent data.

51. The method of claim 50, wherein said adjusting is done automatically in a feedback loop.

52. The method of claim 35, wherein said activating results in production of SAW selected from the group consisting of: Rayleigh waves, "pseudo" Rayleigh waves, and Lamb waves.

53. The method of claim 52, wherein said production of SAW results in elliptical motion on a surface of the device.

54. The method of claim 53, wherein said elliptical motion is produced in multiple directions.

55. The method of claim 52, wherein said producing said SAW comprises producing waves with a spectrum plot in a range of 0.01-10 MHz.

56. The method of claim 52, wherein said producing said SAW comprises producing waves with amplitudes in a range of 1-50 nanometers.

57. The method of claim 35, further comprising providing conventional ultrasound to the medical device to enhance disruption of bacterial adhesion.

58. The method of claim 35, wherein said activating causes production of SAW and further causes particles on the surface of the device to move in a direction which is opposite to a direction of surface acoustic wave propagation.

59. The method of claim 35, further comprising providing electrical current simultaneously with said activating.

60. The method of claim 35, wherein the medical device is an indwelling medical device.

61. The method of claim 60, wherein said providing an actuator comprises connecting said actuator to an external portion of said indwelling medical device.

\* \* \* \* \*